United States Patent [19]
Kool

[11] Patent Number: 5,426,180
[45] Date of Patent: Jun. 20, 1995

[54] METHODS OF MAKING SINGLE-STRANDED CIRCULAR OLIGONUCLEOTIDES

[75] Inventor: Eric T. Kool, Rochester, N.Y.

[73] Assignee: Research Corporation Technologies, Inc., Tucson, Ariz.

[21] Appl. No.: 4,800

[22] Filed: Jan. 11, 1993

Related U.S. Application Data

[63] Continuation-in-part of Ser. No. 859,922, Mar. 26, 1992, abandoned, which is a continuation-in-part of Ser. No. 675,843, Mar. 27, 1991, abandoned.

[51] Int. Cl.[6] .................. C07H 21/02; C07H 21/04
[52] U.S. Cl. ................... 536/25.3; 536/24.3; 536/24.5; 536/24.31; 536/24.32
[58] Field of Search .............. 536/25.3, 24.3, 24.31, 536/24.32, 24.5

[56] References Cited

U.S. PATENT DOCUMENTS

| | | | |
|---|---|---|---|
| 4,766,062 | 8/1988 | Diamond et al. | 435/6 |
| 5,176,996 | 1/1993 | Hogan et al. | 435/6 |

OTHER PUBLICATIONS

Lehninger, "*Principles of Biochemistry*", Worth Publishers, N.Y., 1982, p. 800.

Agrawal, et al. (1988), "Oligodeoxynucleoside Phosphoramidates and Phosphorothioates as Inhibitors of Human Immunodeficiency Virus," *Proc. Natl. Acad. Sci. USA* 85: 7079–7083.

Baumann, et al. (1988), "Interaction of DNA Hairpin Loops and a Complementary Strand by a Triplet of Base Pairs," *Biochem. Biophys. Res. Commun.* 157: 986–991.

Cooney, et al. (1988), "Site-Specific Oligonucleotide Binding Represses Transcription of the Human c-myc Gene in Vitro," *Science* 241: 456–459.

Durand, et al. (1992), "Triple-Helix Formation by an Oligonucleotide Containing One (dA)$_{12}$ and Two (dT)$_{12}$ Sequences Bridged by Two Hexaethylene Glycol Chains," *Biochemistry* 31: 9197–9204.

Erie, et al. (1989), "Melting Behavior of a Covalently Closed, Single-Stranded, Circular DNA," *Biochemistry* 28: 268–273.

Giovannangeli, et al. (1991), "Single-Stranded DNA as a Target for Triple-Helix Formation," *J. Am. Chem. Soc.* 113: 7775–7777.

Goodchild, et al. (1988), "Inhibition of Human Immunodeficiency Virus Replication by Antisense Oligodeoxynucleotides," *Proc. Natl. Acad. Sci. USA* 85: 5507–5511.

(List continued on next page.)

*Primary Examiner*—Margaret Parr
*Assistant Examiner*—Kenneth R. Horlick
*Attorney, Agent, or Firm*—Scully, Scott, Murphy & Presser

[57] ABSTRACT

The present invention provides single-stranded circular oligonucleotides each with at least one parallel binding (P) domain and at least one corresponding anti-parallel binding (AP) domain separated from each other by loop domains. When more than one P or AP domain is included in a circular oligonucleotide of the present invention, the additional P or AP domains can constitute loop domains for a pair of corresponding P and AP domains, and vice versa. Each P and AP domain has sufficient complementarity to bind to one strand of a defined nucleic acid target wherein the P domain binds in a parallel manner to the target and the corresponding AP domain binds in an anti-parallel manner to the target. Moreover, the present single-stranded circular oligonucleotides can bind to both single-stranded and double-stranded target nucleic acids. The present invention also provides methods of making and using these oligonucleotides as well as kits and pharmaceutical compositions containing these oligonucleotides.

6 Claims, 15 Drawing Sheets

OTHER PUBLICATIONS

Griffin, et al. (1989), "Recognition of Thymine-Adenine Base Pairs by Guanine in a Pyrimidine Triple Helix Motif," *Science* 245: 967–971.

Lee, et al. (1984), "Poly(pyrimidine)-Poly(purine) Synthetic DNA's Containing 5-methylcytosine Form Stable Triplexes at Neutral pH," *Nucleic Acids Research* 12: 6603–6614.

Luebke, et al. (1989), "Nonenzymatic Ligation of Oligodeoxyribonucleotides on a Duplex DNA Template by Triple-Helix Formation," *J. Am. Chem. Soc.* 111: 8733–8735.

Mendel, et al. (1987), "Hoogsteen Base Pairs Proximal and Distal to Echinomycin Binding Sites on DNA," *Proc. Natl. Acad. Sci. USA* 84: 910–914.

Povsic, et al. (1989), "Triple Helix Formation by Oligonucleotides on DNA Extended to the Physiological pH Range," *J. Am. Chem. Soc.* 111: 3059–3061.

Riordan, et al. (1991), "Oligonucleotide-Based Therapeutics," *Nature* 350: 442–443.

Uhlmann, et al. (1990), "Antisense Oligonucleotides: A New Therapeutic Principle," *Chemical Reviews* 90: 543–584.

Vroom, et al. (1988), "Synthesis of Cyclic Oligonucleotides by a Modified Phosphotriester Approach," *Nucleic Acids Research* 18: 4607–4620.

Xodo, et al. (1990), "Spectroscopic and Calorimetric Investigation on the DNA Triplex Formed by d(CTCTTCTTTCTTTTCTTTCTTCTC) and d(GAGAAGAAAGA) at Acidic pH," *Nucleic Acids Research* 18: 3557–3564.

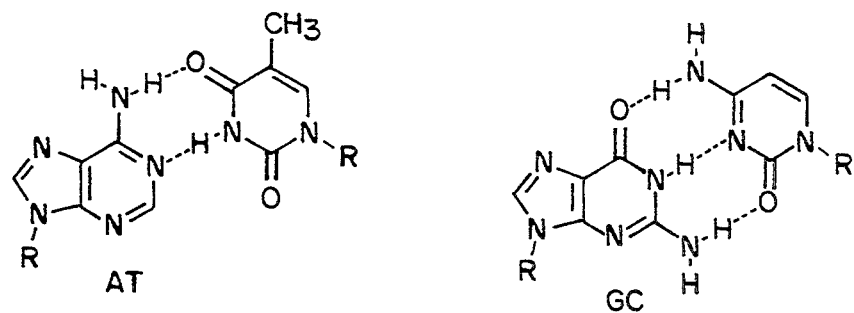
FIG. IA. Watson-Crick Base Pairs: A-T and G-C
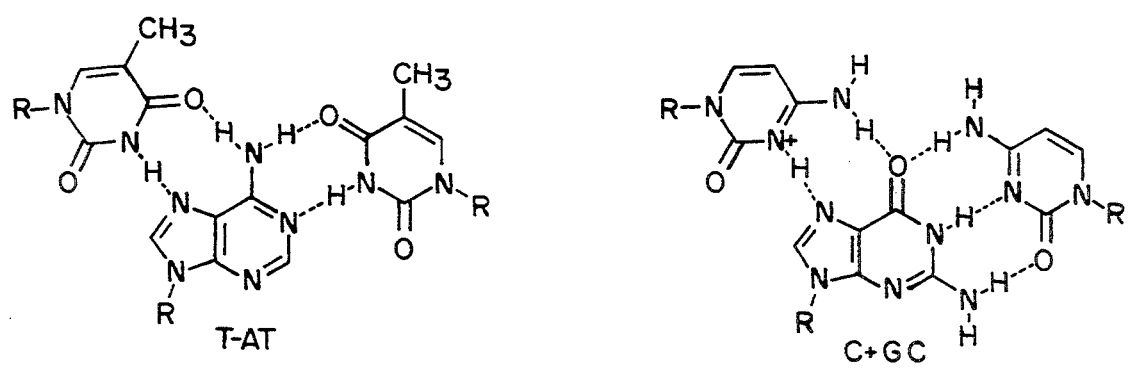
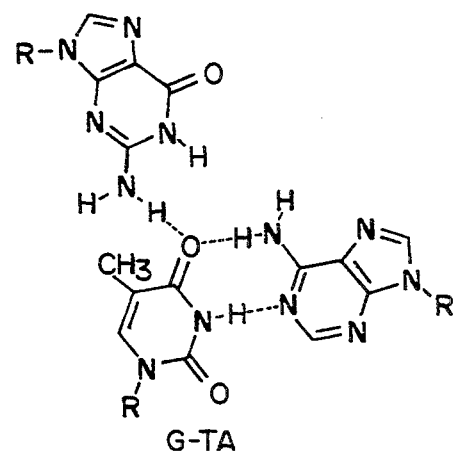
FIG. IB. Base Triads: T-AT, C-GC and G-TA 1  5'-TTTTTTCACACTTTTTTTTTTTCACACTTTTTT (SEQ ID NO: 5)

2  5'-TCTTTCCACACCTTTCTTTTCTTCACACTTCTTT (SEQ ID NO: 6)

3  5'-TTTCTTCACACTTCTTTTCTTTCCACACCTTTCT (SEQ ID NO: 7)

4  5'-AAAAAAAAAAAA (SEQ ID NO: 8)

5  5'-AAGAAAAGAAAG (SEQ ID NO: 9)

6
```
            |
      TTTTTTTTTTTT
    C              C
  A                  A
  C                  C
  A                  A
    C              C
      TTTTTTTTTTTT
```
(SEQ ID NO: 5)

7
```
            |
      CTTCTTTTCTTTCC
    A              A
  C                  C
    A              A
      CTTCTTTTCTTTCC
```
(SEQ ID NO: 6)

8
```
       CTTCTTTTCTTTCC
      A              A
    C                  C
      A              A
       CTTCTTTTCTTTCC
            |
```
(SEQ ID NO: 7)

FIG.3

9  5'-CTTTCTTTTCTT  (SEQ ID NO: 10)

5'-AAGAATAGAAAG  (SEQ ID NO: 11)

5'-AAGAAUAGAAAG  (SEQ ID NO: 12)

5'-CTTTCTATTCTT  (SEQ ID NO: 13)

(SEQ ID NO: 14)

```
    TTCTTCTCTTTC
   C              C
  A                A
 C                  C
  A                A
   C              C
    TTCTTATCTTTC
```

5'-AAAAAAAAAAAA  (SEQ ID NO: 15)
3'-TTTTTTTTTTTT

5'-TCTCTTTTTTTTTTTCTCTCTCTTTTTTTTTTTCTC
(SEQ ID NO: 16)

5'-AAAGAGAGAGAAA  (SEQ ID NO: 17)

(SEQ ID NO: 18)

```
      TTTTTTTTT
   T            T
  C              C
 T                T
 C                C
 T                T
 C                C
 T                T
  C              C
   T            T
      TTTTTTTTT
```

5'-AGAGAGAGA  (SEQ ID NO: 19)

5'-AAAAAAAAA  (SEQ ID NO: 20)

5'-CACAAGAGAGAGAATCCCTAAAAAAAAAAACAC (SEQ ID NO: 21)

5'-TCTCTCTCT  (SEQ ID NO: 22)

5'-TTTTTTTTT  (SEQ ID NO: 23)

FIG.3(con't)

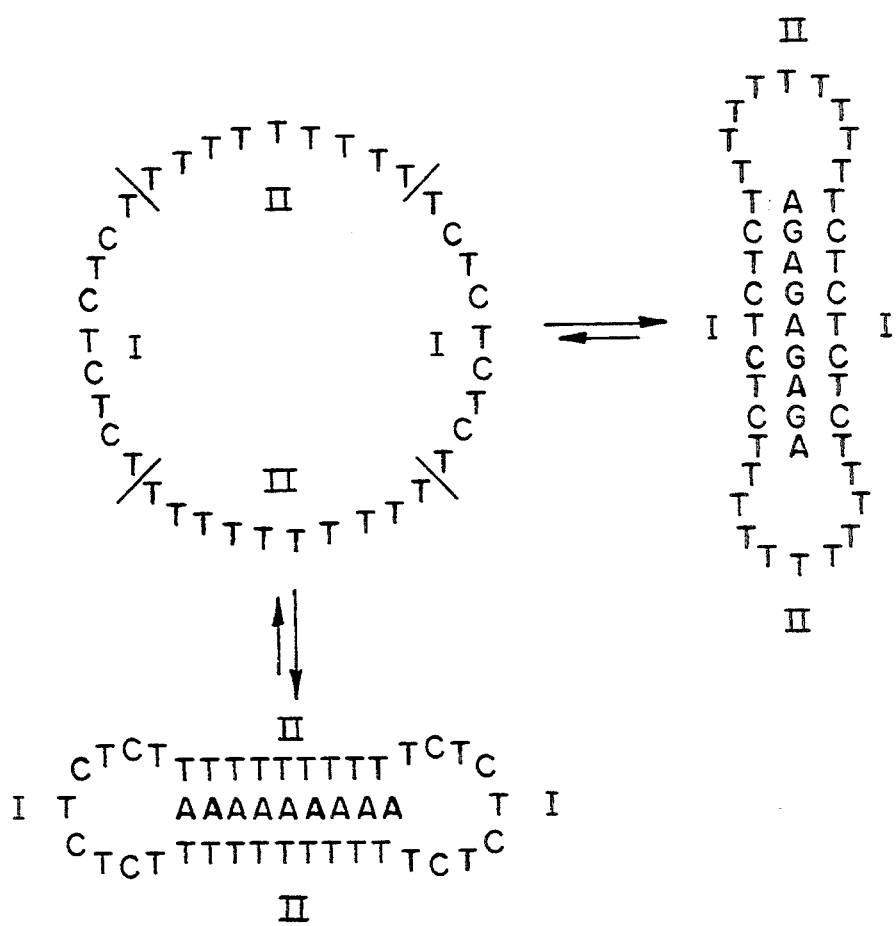
FIG.IIA
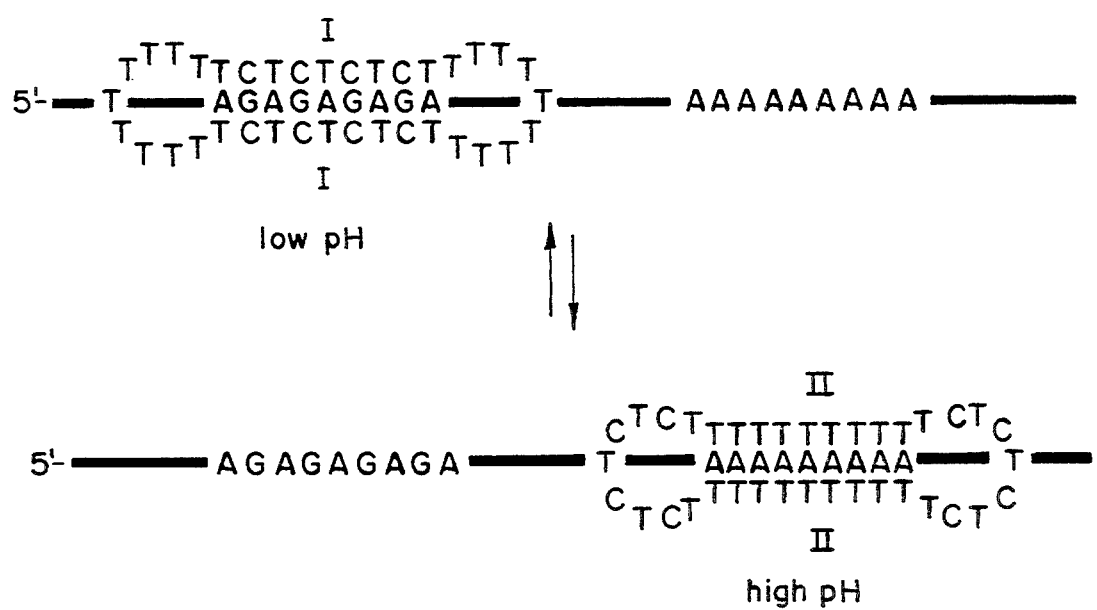
FIG.IIB

METHODS OF MAKING SINGLE-STRANDED CIRCULAR OLIGONUCLEOTIDES

This invention was made with United States government support under grant number GM-46625 awarded by the National Institutes of Health. The United States government has certain rights in the invention.

The present application is a continuation-in-part of copending U.S. Ser. No. 859,922 filed Mar. 26, 1992 and now abandoned which is a continuation-in-part of U.S. Ser. No. 675,843 filed Mar. 27, 1991 and now abandoned. The subject matter of the present application relates to subject matter contained in Disclosure Document number 234,794 received by the United States Patent and Trademark Office on Sep. 5, 1989.

FIELD OF THE INVENTION

The present invention provides single-stranded circular oligonucleotides capable of binding to a target DNA or RNA and thereby regulating DNA replication, RNA transcription, protein translation, and other processes involving nucleic acid templates. Furthermore, circular oligonucleotides can be labeled for use as probes to detect or isolate a target nucleic acid. Circular oligonucleotides can also displace one strand of a duplex nucleic acid without prior denaturation of the duplex. Moreover, circular-oligonucleotides are resistant to exonucleases and bind to a target with higher selectivity and affinity than do linear oligonucleotides.

BACKGROUND OF THE INVENTION

An oligonucleotide binds to a target nucleic acid by forming hydrogen bonds between bases in the target and the oligonucleotide. Common B DNA has conventional adenine-thymine (A-T), and guanine-cytosine (G-C) Watson and Crick base pairs with two and three hydrogen bonds, respectively. Conventional hybridization technology is based upon the capability of sequence-specific DNA or RNA probes to bind to a target nucleic acid via Watson-Crick hydrogen bonds. However, other types of hydrogen bonding patterns are known wherein some atoms of a base which are not involved in Watson-Crick base pairing can form hydrogen bonds to another nucleotide. For example, thymine (T) can bind to an A-T Watson-Crick base pair via hydrogen bonds to the adenine, thereby forming a T-AT base triad. Hoogsteen (1959, Acta Crystallography 12: 822) first described the alternate hydrogen bonds present in T-AT and C-GC base triads. More recently, G-TA base triads, wherein guanine can hydrogen bond with a central thymine, have been observed (Griffin et al., 1989, Science 245: 967–971). If an oligonucleotide could bind to a target with both Watson-Crick and alternate hydrogen bonds an extremely stable complex would form that would have a variety of in vivo and in vitro utilities. However, to date there has been no disclosure of an oligonucleotide with the necessary structural features to achieve stable target binding with both Watson-Crick and alternate hydrogen bonds.

Oligonucleotides have been observed to bind by non-Watson-Crick hydrogen bonding in vitro. For example, Cooney et al., 1988, Science 241:456 disclose a 27-base single-stranded oligonucleotide which bound to a double-stranded nucleic acid via non-Watson-Crick hydrogen bonds. However, triple-stranded complexes of this type are not very stable, because the oligonucleotide is bound to its target only with less stable alternate hydrogen bonds, i.e., without any Watson-Crick bonds.

Oligonucleotides have been used for a variety of utilities. For example, oligonucleotides can be used as probes for target nucleic acids that are immobilized onto a filter or membrane, or are present in tissues. Sambrook et al. (1989, Molecular Cloning: A Laboratory Manual, Vols. 1–3, Cold Spring Harbor Press, N.Y.) provide a detailed review of hybridization techniques.

Furthermore, there has been great interest recently in developing oligonucleotides as regulators of cellular nucleic acid biological function. This interest arises from observations on naturally occurring complementary, or antisense, RNA used by some cells to control protein expression. However, the development of oligonucleotides for in vivo regulation of biological processes has been hampered by several long-standing problems, including the low binding stability and nuclease sensitivity of linear oligonucleotides.

For example, transcription of the human c-myc gene has been inhibited in a cell free, in vitro assay system by a 27-base linear oligonucleotide designed to bind to the c-myc promoter. Inhibition was only observed using a carefully controlled in vitro assay system wherein lower than physiological temperatures were employed, and many cellular enzymes had been removed or inactivated. These conditions were necessary because linear oligonucleotides bind with low affinity and are highly susceptible to enzymes which degrade linear pieces of DNA (Cooney et al.). Splicing of a pre-mRNA transcript essential for Herpes Simplex virus replication has also been inhibited with a linear oligonucleotide which was complementary to an acceptor splice junction. In this instance, a methylphosphonate linkage was employed in the linear oligonucleotide to increase its nuclease resistance. Addition of this chemically-modified oligonucleotide to the growth medium caused reduction in protein synthesis and growth of uninfected cells, most likely because of toxicity problems at high concentrations (Smith et al., 1986, Proc. Natl. Acad. Sci. USA 83: 2787–2791).

In another example, linear oligonucleotides were used to inhibit human immunodeficiency virus replication in cultured cells. Linear oligonucleotides complementary to sites within or near the terminal repeats of the retrovirus genome and within sites complementary to certain splice junctions were most effective in blocking viral replication. However, these experiments required large amounts of the linear oligonucleotides before an effect was obtained, presumably because of the low binding stability and vulnerability of these linear oligonucleotides to nucleases (Goodchild et al., 1988, Proc. Natl. Acad. Sci. USA 85: 5507–5511).

Accordingly, oligonucleotides that are useful as regulators of biological processes preferably possess certain properties. First, the oligonucleotide should bind strongly enough to its complementary target nucleic acid to have the desired regulatory effect. Second, it is generally desirable that the oligonucleotide and its target be sequence specific. Third, the oligonucleotide should have a sufficient half-life under in vivo conditions for it to be able to accomplish its desired regulatory action in the cell. Hence, the oligonucleotide should be resistant to enzymes that degrade nucleic acids, e.g. nucleases. Fourth, the oligonucleotide should be able to bind to single- and double-stranded targets.

While linear oligonucleotides may satisfy the requirement for sequence specificity, linear oligonucleotides are sensitive to nucleases and generally require chemical modification to increase biological half-life. Such modifications increase the cost of making an oligonucleotide and may present toxicity problems. Furthermore, linear oligonucleotides bind to form a two-stranded complex like those present in cellular nucleic acids. Consequently, cellular enzymes can readily manipulate and dissociate a linear oligonucleotide bound in a double-stranded complex with target. The low binding strength and nuclease sensitivity of linear oligonucleotides can thus necessitate administration of high concentrations of oligonucleotide, in turn making such administration toxic or costly. Moreover, while linear oligonucleotides can bind to a double-stranded target via alternate hydrogen bonds (e.g. Hoogsteen binding), linear oligonucleotides cannot readily dissociate a double-stranded target to replace one strand and thereby form a more stable Watson-Crick bonding pattern.

Furthermore, increased binding strength increases the effectiveness of a regulatory oligonucleotide. Therefore, an oligonucleotide with high binding affinity can be used at lower dosages. Lower dosages decrease costs and reduce the likelihood that a chemically-modified oligonucleotide will be toxic. Therefore, high oligonucleotide binding affinity for target is a highly desirable trait.

Accordingly, the present invention provides single-stranded circular oligonucleotides which, by nature of the circularity of the oligonucleotide and the domains present on the oligonucleotide, are nuclease resistant and bind with strong affinity and high selectivity to their targeted nucleic acids. Moreover, the present circular oligonucleotides can dissociate and bind to a double-stranded target without prior denaturation of that target.

Some types of single-stranded circles of DNA or RNA are known. For example, the structures of some naturally occurring viral and bacteriophage genomes are single-stranded circular nucleic acids. Single-stranded circles of DNA have been studied by Erie et al. (1987, Biochemistry 26:7150–7159 and 1989, Biochemistry 28: 268–273). However, none of these circular molecules are designed to bind a target nucleic acid. Hence, the present invention represents an innovation characterized by a substantial improvement relative to the prior art since the subject circular oligonucleotides exhibit high specificity, low or no toxicity and more resistance to nucleases than linear oligonucleotides, while binding to single- or double-stranded target nucleic acids more strongly than conventional linear oligonucleotides.

SUMMARY OF THE INVENTION

The present invention provides a single-stranded circular oligonucleotide having at least one parallel binding (P) domain and at least one anti-parallel binding (AP) domain, and having a loop domain between each binding domain to form the circular oligonucleotide. Each P and corresponding AP domain has sufficient complementarity to bind detectably to one strand of a defined nucleic acid target with the P domain binding in a parallel manner to the target, and the AP domain binding in an anti-parallel manner to the target. Sufficient complementarity means that a sufficient number of base pairs exists between the target nucleic acid and the P and/or AP domains of the circular oligonucleotide to achieve stable, i.e. detectable, binding.

In the case where multiple P and AP binding domains are included in the circular oligonucleotides of the present invention, the loop domains separating the P and AP binding domains can constitute, in whole or in part, another P or AP domain which functions as a binding domain in an alternate conformation. In other words, depending upon the particular target, a binding domain (P or AP) can also function as a loop domain for another binding domain and vice versa.

Another aspect of the present invention provides the subject single-stranded circular oligonucleotides derivatized with a reporter molecule to provide a probe for a target nucleic acid, or with a drug or other pharmaceutical agent to provide cell specific drug delivery, or with agents which can cleave or otherwise modify the target nucleic acid or, furthermore, with agents that can facilitate cellular uptake or target binding of the oligonucleotide.

An additional aspect of the present invention provides single-stranded circular oligonucleotides linked to a solid support for isolation of a nucleic acid complementary to the oligonucleotide.

Another aspect of the present invention provides a compartmentalized kit for detection or diagnosis of a target nucleic acid including at least one first container providing any one of the present circular oligonucleotides.

A further aspect of the present invention provides a method of detecting a target nucleic acid which involves contacting a single-stranded circular oligonucleotide with a sample containing the target nucleic acid, for a time and under conditions sufficient to form an oligonucleotide-target complex, and detecting the complex. This detection method can be by fluorescent energy transfer.

A still further aspect of the present invention provides a method of regulating biosynthesis of a DNA, an RNA or a protein. This method includes contacting at least one of the subject circular oligonucleotides with a nucleic acid template for the DNA, the RNA or the protein under conditions sufficient to permit binding of the oligonucleotide to a target sequence contained in the template, followed by binding of the oligonucleotide to the target, blocking access to the template and thereby regulating biosynthesis of the DNA, the RNA or the protein.

An additional aspect of the present invention provides pharmaceutical compositions for regulating biosynthesis of a nucleic acid or protein containing a biosynthesis regulating amount of at least one of the subject circular oligonucleotides and a pharmaceutically acceptable carrier.

A further aspect of the present invention provides a method of preparing a single-stranded circular oligonucleotide which includes binding a linear precircle to an end-joining-oligonucleotide, joining the two ends of the precircle and recovering the circular oligonucleotide product.

Another aspect of the present invention provides a method of strand displacement in a double-stranded nucleic acid target by contacting the target with any one of the present circular oligonucleotides for a time and under conditions effective to denature the target and to bind the circular oligonucleotide.

DESCRIPTIONS OF THE DRAWINGS:

FIG. 1A depicts the bonding patterns of Watson-Crick (anti-parallel domain) AT and GC base pairs. FIG. 1B depicts T-AT, C+GC and G-TA base triads that can form between P, target and AP nucleotides.

FIG. 2 schematically illustrates a circularization reaction for synthesis of single-stranded circular oligonucleotides. A linear precircle oligonucleotide is bound to an oligonucleotide having the same sequence as the target, i.e. an end-joining-oligonucleotide, to form a precircle complex. After ligation, the circularized oligonucleotides are separated from the end-joining-oligonucleotide.

FIG. 3 depicts the sequence of linear precursors to circular oligonucleotides, i.e. precircles (1–3 having SEQ ID NO: 5, SEQ ID NO: 6 and SEQ ID NO: 7), targets (4,5 having SEQ ID NO: 8 and SEQ ID NO: 9), circular oligonucleotides (6,7,8 and 13 having SEQ ID NO: 5–7 and 14), and linear oligonucleotides (9–12 and 14 having SEQ ID NO: 10–13 and 15) described in the examples.

FIG. 4 depicts the structure of a linear precircle complexed with an end-joining-oligonucleotide before ligation.

FIG. 5 depicts the effect of pH on circular oligonucleotide:target complex formation as measured by Tm. Filled circles represent the stability at different pH values for a 6:4 complex while filled squares depict the stability of a 7:5 complex. The sequences of circular oligonucleotides 6 and 7 and targets 4 and 5 are presented in FIG. 3.

Figure 9:
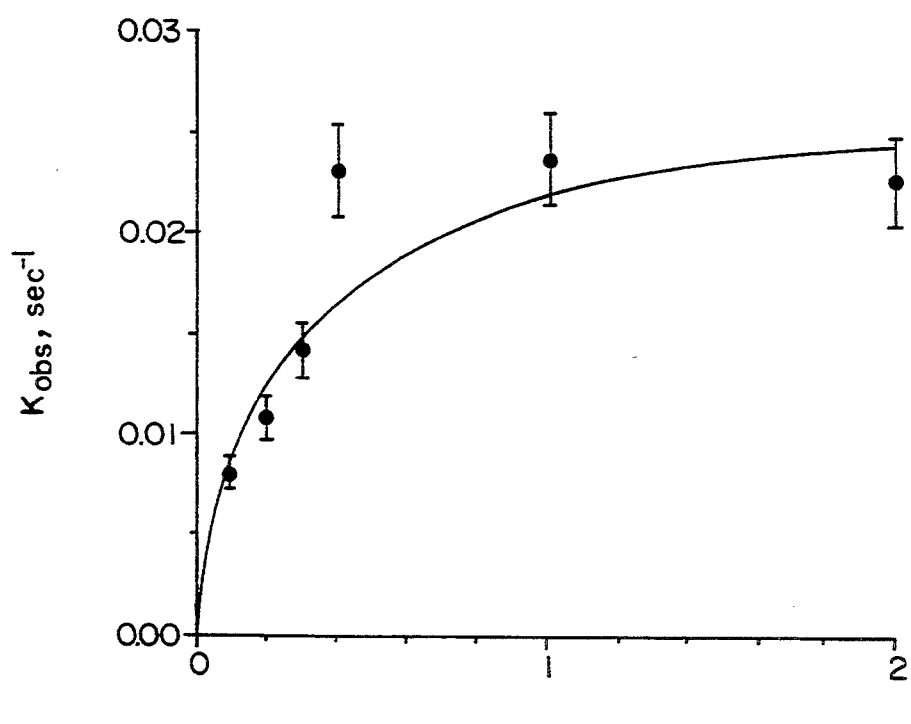

FIG. 9 depicts a plot of observed pseudo-first rate constant, $K_{obs}$ for duplex target (SEQ ID NO: order rate constant, $K_{obs}$ for duplex target (SEQ ID NO: 5) at several concentrations. Uncertainty in rate constants are no more than ±10%. The depicted curve is a rectangular hyperbola generated as a best fit. A double reciprocal plot of the data, i.e., [circular oligonucleotide]$^{-1}$ vs $(K_{obs})^{-1}$ is linear with a slope of $8.95 \times 10^{-6}$ sec.M$^{-1}$ and a y-intercept of 39.8 sec.

Figure 10A:
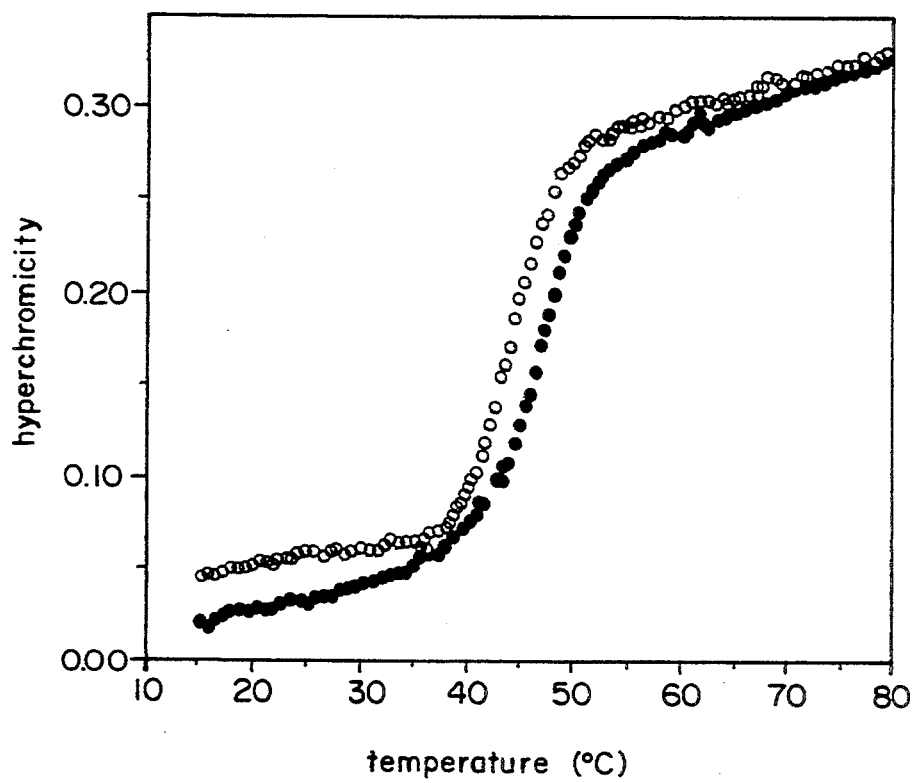

FIG. 10A depicts plots of the observed hyperchromicity (at 260 nm) as the temperature is increased for a circular oligonucleotide having two sets of binding domains and SEQ ID NO:18 when bound to either a target oligonucleotide having SEQ ID NO:19 (open circles) or to a target oligonucleotide having SEQ ID NO:20 (filled circles). These data indicate the melting temperature ($T_m$) of the SEQ ID NO:18-SEQ ID NO:19 complex is 44.5° C. and the $T_m$ of the SEQ ID NO:18-SEQ ID NO:20 complex is 47.5° C.

Figure 10B:
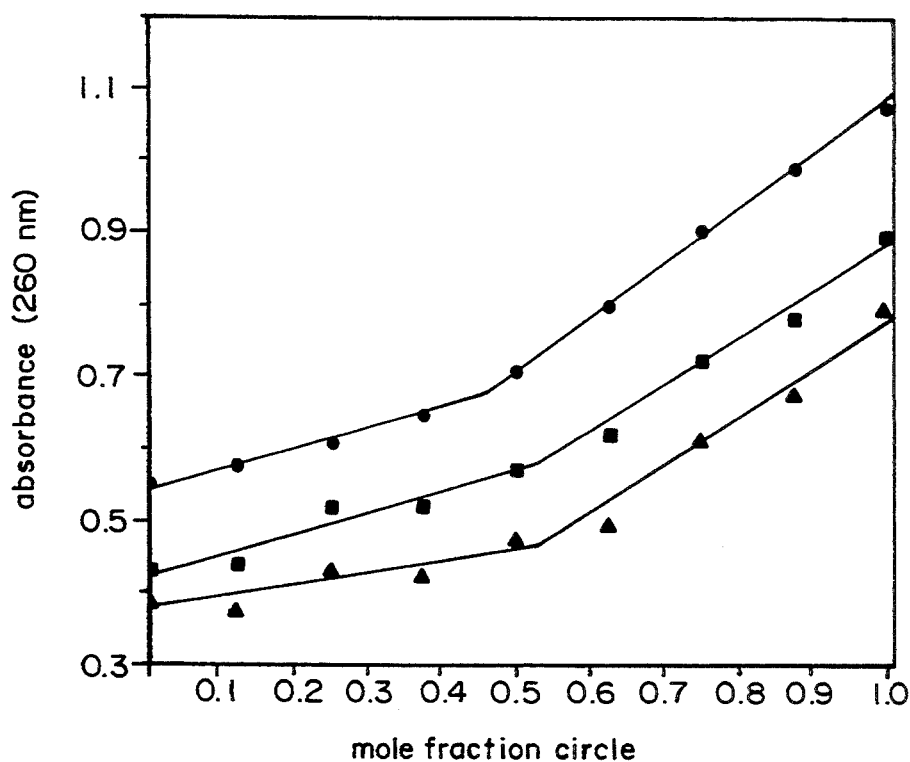

FIG. 10B depicts the mole fraction present of the (SEQ ID NO:18) circular oligonucleotide having two pairs of binding domains versus the absorbance, when mixed with the SEQ ID NO:19 target (squares), the SEQ ID NO:20 target (triangles) or when mixed with a 1:1 combination both SEQ ID NO:19 and SEQ ID NO:20 targets (circles). The inflection point of the observed absorbance provides the mole fraction of SEQ ID NO:18 circular oligonucleotide needed for complete complexation with the indicated target oligonucleotides.

FIG. 11A is a schematic diagram illustrating the binding of a SEQ ID NO:18 circular oligonucleotide having two pairs of binding domains, i.e. I and II, with either of target oligonucleotide SEQ ID NO:19 or target oligonucleotide SEQ ID NO:20. This figure illustrates that when binding domain pair I has bound its target oligonucleotide, the P and AP domains of pair II serve as loop domains separating the P and AP binding domains of pair I, and vice versa.

FIG. 11B is a schematic diagram illustrating the effect of pH upon target selection by the SEQ ID NO:18 circular oligonucleotide which has two pairs of binding domains, i.e. I and II. In this case two target sites, complementary to the pair I and pair II binding domains, are present within a single oligonucleotide. When the pH is low, pair I binding domains which contain cytosine, preferentially bind to their complementary target, while the pair II binding domains which contain no cytosine, do not bind their target. However, when the pH is high, pair II binding domains containing no cytosine, preferentially bind to their target while the pair I binding domains remain unbound.

Figure 12:
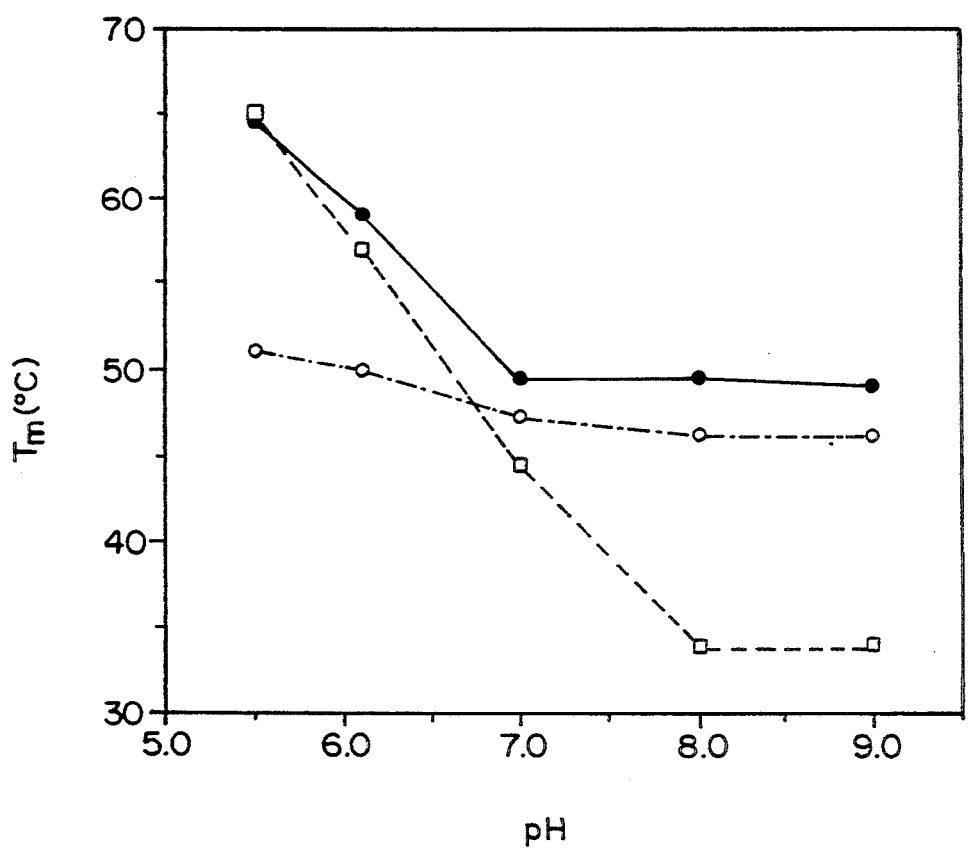

FIG. 12 depicts the melting temperature ($T_m$) as a function of pH when the two binding domain SEQ ID NO:18 circular oligonucleotide is bound to target oligonucleotide SEQ ID NO:20 (open circles), SEQ ID NO:19 (open squares) or SEQ ID NO:21 (filled circles). Oligonucleotides having SEQ ID NO:19 or SEQ ID NO:20 had a single target for the SEQ ID NO:18 circular oligonucleotide, however the oligonucleotide having SEQ ID NO:21 encoded two separate target sites for the SEQ ID NO:18 circular oligonucleotide.

Figure 13A:
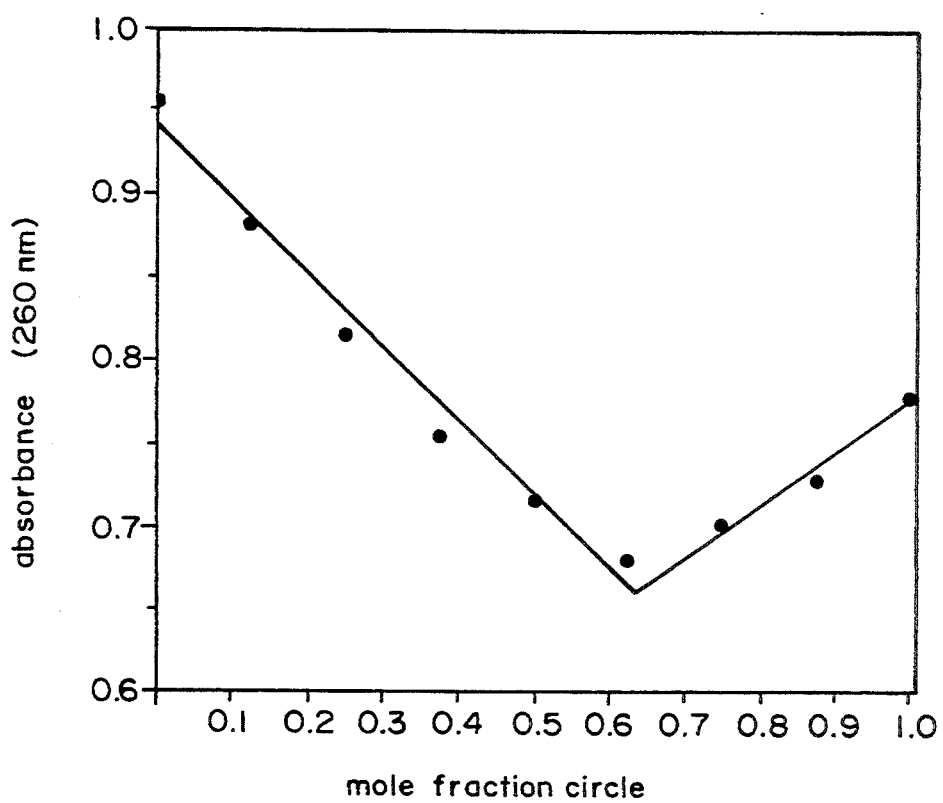

FIG. 13A depicts the absorbance versus mole fraction of SEQ ID NO:18 circular oligonucleotide present in a mixture with the longer two-target site oligonucleotide having SEQ ID NO:21. The mole fraction of circular oligonucleotide at complete complexation (inflection point in the observed absorbance) is about 0.63.

Figure 13B:
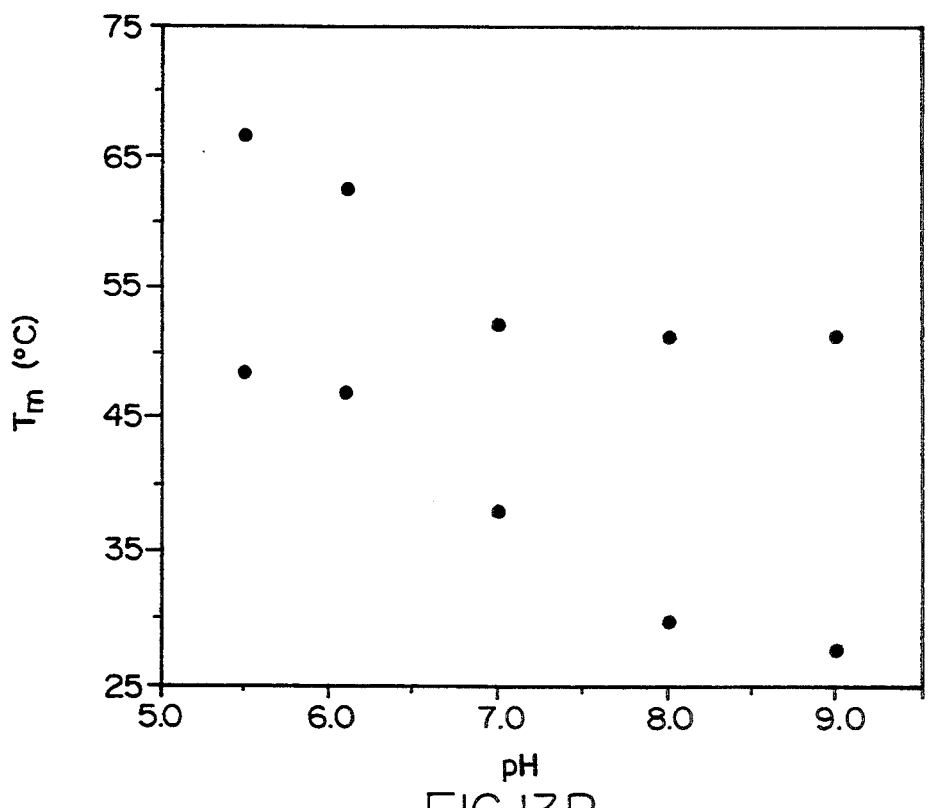

FIG. 13B depicts the observed $T_m$ values for the SEQ ID NO:18 circular oligonucleotide bound to the two target-site oligonucleotide having SEQ ID NO:21. As shown, there were two $T_m$ values at each of the pH values tested. These two $T_m$ values correspond to separate melting events at each of the two target sites within the SEQ ID NO:21 oligonucleotide.

Figure 14A:
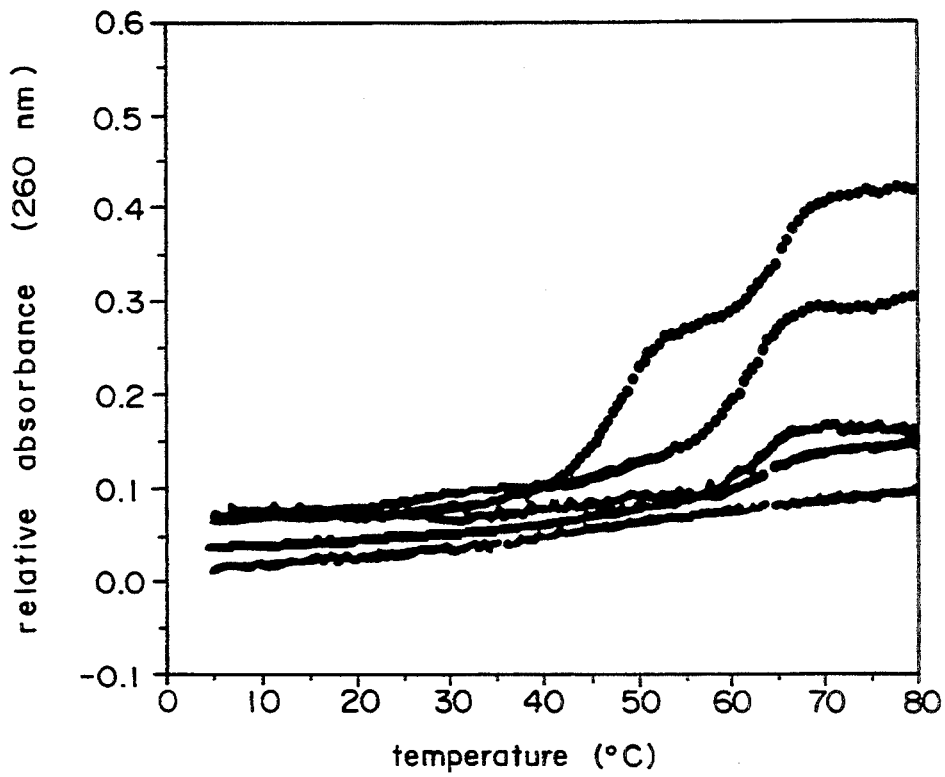

FIG. 14A depicts the relative absorbance at 260 nm of increasing amounts of the SEQ ID NO:18 circular oligonucleotide bound to the two-target site SEQ ID NO:21 oligonucleotide at pH 5.5. The SEQ ID NO:21 oligonucleotide was present at 1.5 µM and the SEQ ID NO:18 circular oligonucleotide concentration was present at 0, 0.25, 0.5, 1.0 and 2.0 molar equivalents (lower to upper curves, respectively). The temperature at which the absorbance increases dramatically corresponds to the melting temperature. Only one sharp increase in absorbance was observed at about 60° C. when the circular oligonucleotide was present at 0, 0.25, 0.5 and 1.0 molar equivalents (lower four curves). However, two sharp increases in absorbance were observed at about 47° C. and about 60° C. when 2.0 molar equivalents of circular oligonucleotide were mixed with 1.0 molar equivalents of the SEQ ID NO:21 oligonucleotide.

Figure 14B:
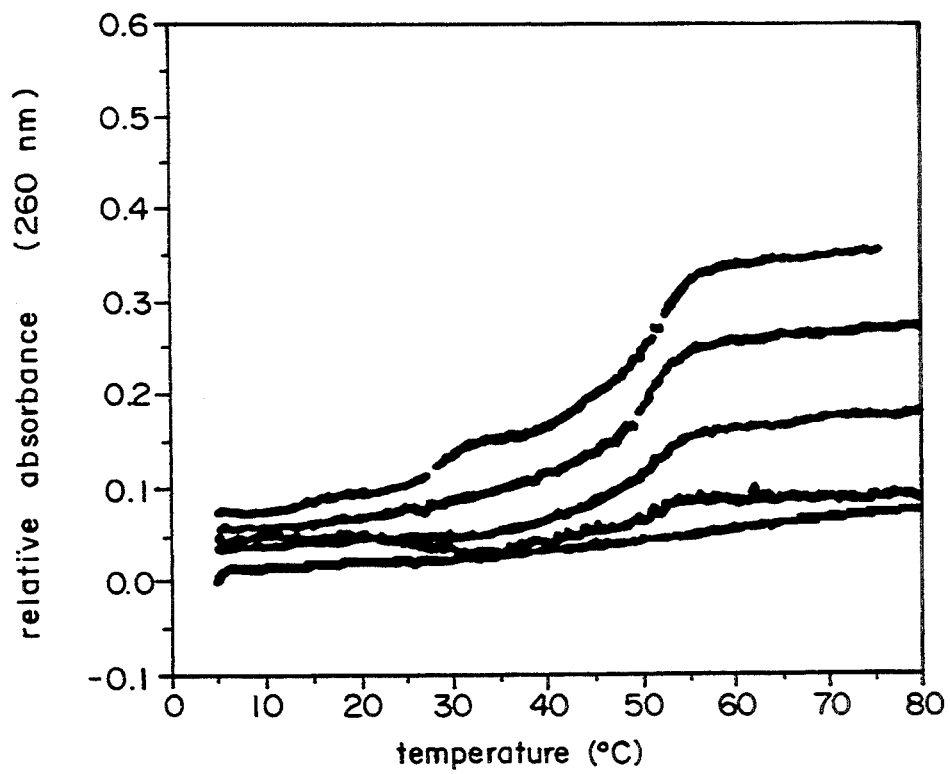

FIG. 14B depicts the relative absorbance at 260 nm of increasing amounts of the SEQ ID NO:18 circular oligonucleotide bound to the two-target site SEQ ID NO:21 oligonucleotide at pH 8.5. The SEQ ID NO:21 oligonucleotide was present at 1.5 µM and the SEQ ID NO:18 circular oligonucleotide concentration was present at 0, 0.25, 0.5, 1.0 and 2.0 molar equivalents (lower to upper curves, respectively). The observed melting points at low molar ratios of circular oligonucleotide to SEQ ID NO:21 oligonucleotide is about 52° C. (FIG. 14B middle three curves middle three curves, corresponding to molar ratios of SEQ ID NO:18 to SEQ ID NO:21 oligonucleotide of 0.25, 0.5 and 1.0).

Figure 15:
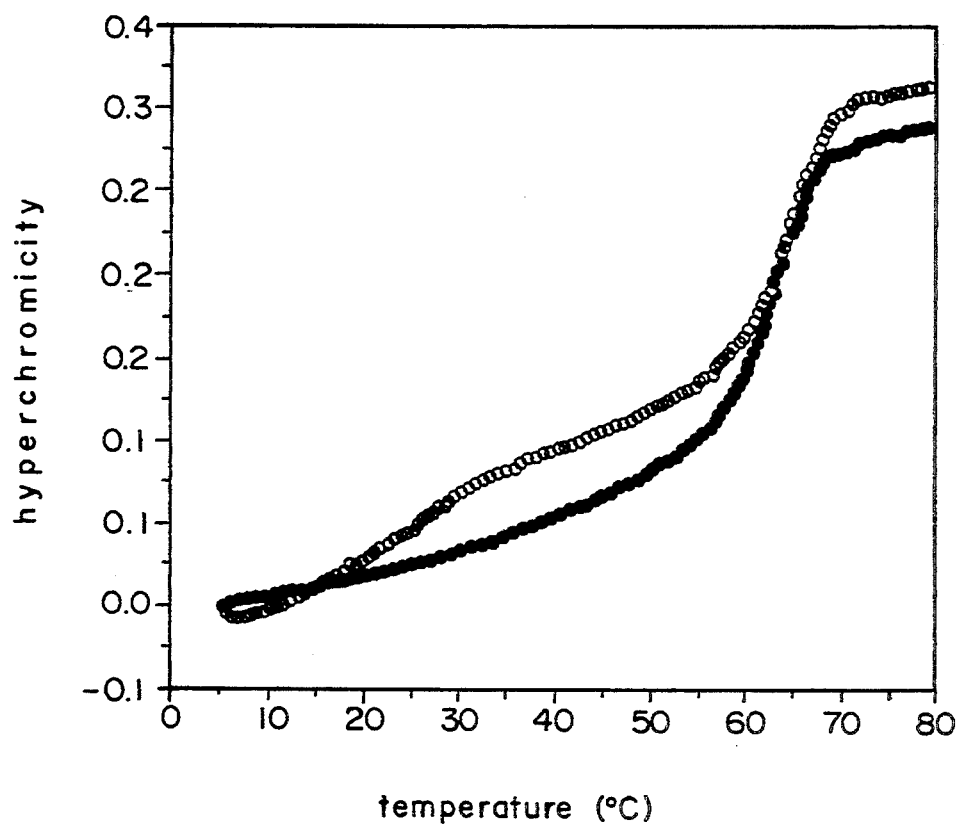

FIG. 15 depicts the hyperchromicity at pH 5.5 of a mixture of circular oligonucleotide (SEQ ID NO:18 at 1.5 µM) with two-target site oligonucleotide (SEQ ID NO:21 at 1.5 µM) in the presence of oligonucleotides having either SEQ ID NO:22 (TCTCTCTCT at 1.5 µM, filled circles) or SEQ ID NO:23 (TTTTTTTTT at 1.5 µM, open circles). Two inflections in hyperchromicity (open circles) indicate that binding has occurred at both target sites within the SEQ ID NO:21 oligonucleotide, whereas a single inflection (filled circles) indicates binding has occurred at only one site in the SEQ ID NO:21 oligonucleotide.

Figure 16:
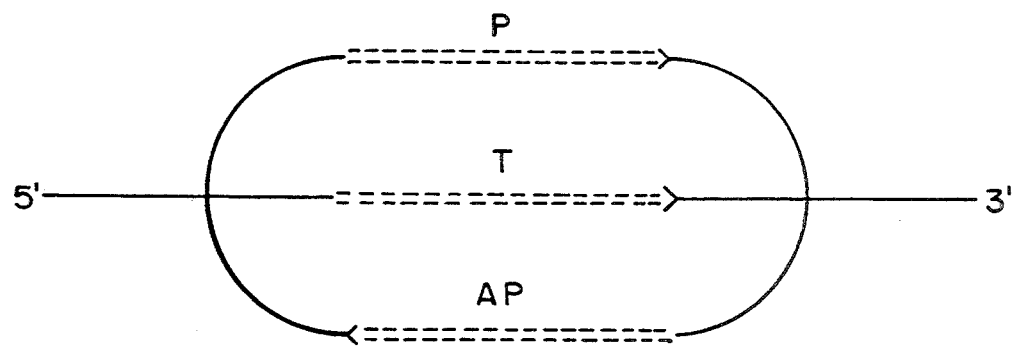

FIG. 16 provides a schematic diagram illustrating the circular arrangement of one set of P and AP domains relative to each other as well as when bound to a target strand (T). The arrows indicate the 5' to 3' orientation of each strand where the 5' end of each domain is the tail and the 3' end is the arrowhead.

DETAILED DESCRIPTION OF THE INVENTION

The present invention relates to single-stranded circular oligonucleotides, i.e. circles, which can bind to nucleic acid targets with higher affinity and selectivity than a corresponding linear oligonucleotide. Moreover, since the present circles can open up two strands of a double-stranded nucleic acid and bind thereto, both single- and double-stranded nucleic acids can be targets for binding by the present circular oligonucleotides.

Furthermore, the strong, selective binding of these circles to either single- or double-stranded targets provides a variety of uses, including methods of regulating such biological processes as DNA replication, RNA transcription, RNA splicing and processing, protein translation and the like. Similarly, the ability of these circles to dissociate double-stranded nucleic acids and to selectively and stably bind to targeted nucleic acids makes them ideal as diagnostic probes or as markers to localize, for example, specific sites in a chromosome or other DNA or RNA molecules. Additionally, the present circles are useful for isolation of complementary nucleic acids or for sequence-specific delivery of drugs or other molecules into cells.

In particular, the single-stranded circular oligonucleotides of the present invention have at least one parallel binding (P) domain and at least one anti-parallel binding (AP) domain and have a loop domain between each binding domain, so that a circular oligonucleotide is formed. Moreover, each P and AP domain exhibits sufficient complementarity to bind to one strand of a defined nucleic acid target with the P domain binding to the target in a parallel manner and the AP domain binding to the target in an anti-parallel manner.

The schematic illustration set forth in FIG. 16 shows the circular arrangement of one set of P and AP oligonucleotide domains relative to each other as well as when bound to a target (T, as indicated in FIG. 16).

The arrows indicate the 5' to 3' orientation of each strand with the 5' end of each domain at the tail and the 3' end at the arrowhead. Hence as used herein binding of nucleic acids in a parallel manner means that the 5' to 3' orientation is the same for each strand or nucleotide in the complex. This is the type of binding present between the target and the P domain. As used herein, binding of nucleic acids in an anti-parallel manner means that the 5' to 3' orientations of two strands or nucleotides in a complex lie in opposite directions, i.e. the strands are aligned as found in the typical Watson-Crick base pairing arrangement of double helical DNA.

When more than one P and AP binding domain is present, such binding domains are separated from other P and AP domains by loop domains whose lengths are sufficient to permit binding to multiple targets. Moreover, when a circular oligonucleotide has multiple AP and P domains, a loop domain for one pair of corresponding AP and P binding domains can constitute an AP or P domain for binding to another target. When a circular oligonucleotide of the present invention includes, e.g., two pairs of corresponding binding domains, these pairs of corresponding binding domains can also bind separate target sites. Moreover, when a circle has multiple AP and P domains, the corresponding targets need not be linked on one nucleic acid strand. Furthermore, a loop domain of a circular oligonucleotide bound to a given target can be an AP or P domain for binding to a second target when the circular oligonucleotide releases from the first target.

In accordance with this invention, the nucleotide sequences of the P and AP domains can be determined from the defined sequence of the nucleic acid target by reference to the base pairing rules provided hereinbelow. A target can be either single- or double-stranded and is selected by its known functional and structural characteristics. For example, some preferred targets can be coding regions, origins of replication, reverse transcriptase binding sites, transcription regulatory elements, RNA splicing junctions, or ribosome binding sites, among others. A target can also be selected by its capability for detection or isolation of a DNA or RNA template. Preferred targets are rich in purines, i.e. in adenines and guanines.

The nucleotide sequence of the target DNA or RNA can be known in full or in part. When the target nucleotide sequence is completely known the sequences of the P and AP domains are designed with the necessary degree of complementarity to achieve binding, as detected by known procedures, for example by a change in light absorption or fluorescence. In some instances, the target sequence can be represented by a consensus sequence or be only partially known. For example, circular oligonucleotides (circles) which bind to an entire class of targets represented by a consensus sequence can be provided by designing the P and AP domains from the target consensus sequence. In this instance some of the targets may match the consensus sequence exactly and others may have a few mismatched bases, but not enough mismatch to prevent binding. Likewise, if a portion of a target sequence is known, one skilled in the art can refer to the base pairing rules provided hereinbelow to design circles which bind to that target with higher affinity than a linear oligonucleotide that has a sequence corresponding to that of the circle.

Thus, the present invention is also directed to circles having P and AP domains which are sufficiently complementary to bind to a nucleic acid target wherein a sufficient number, but not necessarily all, nucleotide positions in the P and AP domains are determined from the target sequence in accordance with the base pairing rules of this invention. The number of determined (i.e. known) positions is that number of positions which are necessary to provide sufficient complementarity for binding of the subject oligonucleotides to their targets, as detected by standard procedures including a change in light absorption upon binding or melting.

The base pairing rules of the present invention provide for the P domain to bind to the target by forming base pairs wherein the P domain and target nucleotides have the same 5' to 3' orientation. In particular, these rules are satisfied to the extent needed to achieve binding of a circular oligonucleotide to its nucleic acid target, i.e. the degree of complementarity need not be 100% so long as binding can be detected. Hence, the general rules for determining the sequence of the P domain are thus:

when a base for a position in the target is guanine or a guanine analog, then P has cytosine, or a suitable analog thereof, in a corresponding position;

when a base for a position in the target is adenine, or an adenine analog then P has thymine or uracil, or suitable analogs thereof, in a corresponding position;

when a base for a position in the target is thymine, or a thymine analog, then P has cytosine or guanine, or suitable analogs thereof, in a corresponding position;

when a base for a position in the target is cytosine, or a cytosine analog, then P has cytosine, thymine or uracil, or suitable analogs thereof, in a corresponding position; and when a base for a position in the target is uracil, or a uracil analog, then P has cytosine, guanine, thymine, or uracil, or suitable analogs thereof, in a corresponding position.

The base pairing rules of the present invention provide for the AP domain to bind to the target by forming base pairs wherein the AP domain and target nucleotides are oriented in opposite directions. In particular these rules are satisfied to the extent necessary to achieve detectable binding of a circular oligonucleotide to its nucleic acid target, i.e. the degree of complementarity can be less than 100%. Hence, the base pairing rules can be adhered to only insofar as is necessary to achieve sufficient complementarity for binding to be detected between the circular oligonucleotide and its target.

Thus, the general rules for determining the sequence of the AP domain are as follows:

when a base for a position in the target is guanine, or a guanine analog, then AP has cytosine or uracil, or suitable analogs thereof, in a corresponding position;

when a base for a position in the target is adenine, or an adenine analog, then AP has thymine or uracil, or suitable analogs thereof, in a corresponding position;

when a base for a position in the target is thymine, or a thymine analog, then AP has adenine, or a suitable analog thereof, in a corresponding position; and when a base for a position in the target is cytosine, or a cytosine analog, then AP has a guanine, or a suitable analog thereof, in corresponding position;

when a base for a position in the target is uracil, or a uracil analog, then AP has adenine or guanine, or suitable analogs thereof, in a corresponding position.

In a preferred embodiment, the P, AP and loop domains are not complementary to each other.

Table 1 summarizes which nucleotides can form anti-parallel base pairs or parallel base pairs with a defined target nucleotide.

TABLE 1

| Target Nucleotide[a] | Anti-Parallel Domain Nucleotide[a] | Parallel Domain Nucleotide[a] |
|---|---|---|
| G | C or U | C |
| A | T or U | T or U |
| T | A | C or G |
| C | G | C, T or U |
| U | A or G | C, G, T or U |

[a]or a suitable analog

Two complementary single-stranded nucleic acids form a stable double helix (duplex) when the strands bind, or hybridize, to each other in the typical Watson-Crick fashion, i.e. via anti-parallel GC and AT base pairs. For the present invention, stable duplex formation and stable triplex formation is achieved when the P and AP domains exhibit sufficient complementarity to the target sequence to achieve stable binding between the circular oligonucleotide and the target molecule. Stable binding occurs when an oligonucleotide remains detectably bound to target under the required conditions.

Complementarity between nucleic acids is the degree to which the bases in one nucleic acid strand can hydrogen bond, or base pair, with the bases in a second nucleic acid strand. Hence, complementarity can sometimes be conveniently described by the percentage, i.e. proportion, of nucleotides which form base pairs between two strands or within a specific region or domain of two strands. For the present invention sufficient complementarity means that a sufficient number of base pairs exist between a target nucleic acid and the P and/or AP domains of the circular oligonucleotide to achieve detectable binding. Moreover, the degree of complementarity between the P domain and the target and the AP domain and the target need not be the same. When expressed or measured by percentage of base pairs formed, the degree of complementarity can range from as little as about 30–40% complementarity to full, i.e. 100%, complementarity. In general, the overall degree of complementarity between the P or AP domain and the target is preferably at least about 50%. However, the P domain can sometimes have less complementarity with the target than the AP domain has with the target, for example the P domain can have about 30% complementarity with the target while the AP domain can have substantially more complementarity, e.g. 50% to 100% complementarity.

Moreover, the degree of complementarity that provides detectable binding between the subject circular oligonucleotides and their respective targets, is dependent upon the conditions under which that binding occurs. It is well known that binding, i.e. hybridization, between nucleic acid strands depends on factors besides the degree of mismatch between two sequences. Such factors include the GC content of the region, temperature, ionic strength, the presence of formamide and types of counter ions present. The effect that these conditions have upon binding is known to one skilled in the art. Furthermore, conditions are frequently determined by the circumstances of use. For example, when a circular oligonucleotide is made for use in vivo, no formamide will be present and the ionic strength, types of counter ions, and temperature correspond to physiological conditions. Binding conditions can be manipulated in vitro to optimize the utility of the present oligonucleotides. A thorough treatment of the qualitative and quantitative considerations involved in establishing binding conditions that allow one skilled in the art to design appropriate oligonucleotides for use under the desired conditions is provided by Beltz et al., 1983, *Methods Enzymol.* 100:266–285 and by Sambrook et al.

Thus for the present invention, one of ordinary skill in the art can readily design a nucleotide sequence for the P and AP domains of the subject circular oligonucleotides which exhibits sufficient complementarity to detectably bind to its target sequence. As used herein "binding" or "stable binding" means that a sufficient amount of the oligonucleotide is bound or hybridized to its target to permit detection of that binding. Binding can be detected by either physical or functional properties of the target:circular oligonucleotide complex.

Binding between a target and an oligonucleotide can be detected by any procedure known to one skilled in the art, including both functional or physical binding assays. Binding may be detected functionally by determining whether binding has an observable effect upon a biosynthetic process such as DNA replication, RNA transcription, protein translation and the like.

Physical methods of detecting the binding of complementary strands of DNA or RNA are well known in the art, and include such methods as DNase I or chemical footprinting, gel shift and affinity cleavage assays and light absorption detection procedures. For example, a method which is widely used, because it is so simple and reliable, involves observing a change in light absorption of a solution containing an oligonucleotide and a target nucleic acid at 220 to 300 nm as the temperature is slowly increased. If the oligonucleotide has bound to its target, there is a sudden increase in absorption at a characteristic temperature as the oligonucleotide and target dissociate or melt.

The binding between an oligonucleotide and its target nucleic acid is frequently characterized by the temperature at which 50% of the oligonucleotide is melted from its target. This temperature is the melting temperature ($T_m$). A higher $T_m$ means a stronger or more stable complex relative to a complex with a lower $T_m$. The stability of a duplex increases with increasing G:C content since G:C base pairs have three hydrogen bonds whereas A:T base pairs have two. The circular oligonucleotides of the present invention provide additional hydrogen bonds and hence more stability since two binding domains are available for bonding to a single target nucleic acid, i.e. the P domain and the AP domain. Hence, the triplex formed by a circular oligonucleotide bound to its target nucleic acid should melt at a higher $T_m$ than the duplex formed by a linear oligonucleotide and a target.

Circular oligonucleotides bind to a nucleic acid target through hydrogen bonds formed between the nucleotides of the binding domains and the target. The AP domain can bind by forming Watson-Crick hydrogen bonds (FIG. 1). The P domain can bind to the target nucleotides by forming non-Watson-Crick hydrogen bonds (e.g., FIG. 1 and Table 1). When two nucleotides from different strands of DNA or RNA hydrogen bond by the base pairing rules defined herein, a base pair or duplex is formed. When a nucleotide from AP and a nucleotide from P both bind to the same target nucleotide, a base triad is formed.

Parallel domain base pairing with a complementary target strand of nucleic acid, is thermodynamically less favorable than Watson-Crick base pairing; however, when both parallel and anti-parallel pairing modes are present in a single molecule, highly stable complexes can form. Thus, two opposing domains of a circular oligomer form a complex with a central target, giving a triplex structure, or a triple helical complex, bounded by the two looped ends of the circle. For example, this arrangement can allow formation of up to four hydrogen bonds when two thymines bind to a target adenine and up to five hydrogen bonds when two cytosines bind to a target guanine.

Furthermore, because of the binding characteristics of the P and AP domains, the present circular oligonucleotides have a higher selectivity for a particular target than do corresponding linear oligonucleotides. At least two factors can contribute to this high selectivity. First, circular oligonucleotides of this invention bind twice to the same central target strand. Hence two domains are involved in selecting a target. Second, protonation of cytosine in a C+G−C triad is favored only when this triad forms and the additional proton gives the triad a positive charge. This positive charge can lessen the negative charge repulsions arising from the juxtapositioning of three phosphodiester backbones.

Protonation of C+G−C triads occurs most readily at low pH and formation of C+G−C triads is favored over formation of many other triads at low pH. Therefore, P and AP domains which are cytosine-rich more stably bind a complementary guanine-rich target at low pH than cytosine-poor P and AP domains bind a guanine-poor target. The skilled artisan can take advantage of the effect of protonation upon C+G−C triad formation to design circular oligonucleotides in accordance with the present invention whose selectivity for a target is enhanced if the pH of the hybridization reaction is known or can be adjusted. This is done simply by selecting a guanine-rich target and constructing cytosine-rich P and AP binding domains if the hybridization pH is low, or by selecting a guanine-poor target and constructing cytosine-poor P and AP binding domains if the hybridization pH is high. For these purposes a low pH is about 5.0 to about 6.8, and preferably about 5.5, whereas a high pH is about 7.0 to about 9.0, and for use in vivo preferably about 7.4. As used herein a cytosine-rich P or AP binding domain has about 2 to about 20 cytosines, and a guanine-rich target has about 2 to about 20 guanines. Conversely, a cytosine-poor P or AP binding domain has no more than one cytosine, while a guanine-poor target has no more than one guanine.

The circular oligonucleotides of the present invention can be constructed to include more than one P or AP binding domain to permit binding of the oligonucleotide to more than one target. The skilled artisan can also select target sites for such multiple-binding domain oligonucleotides which permit construction of cytosine-rich and cytosine-poor pairs of P and AP binding domains. By including a cytosine-rich pair of binding domains with a cytosine-poor pair of binding domains, the skilled artisan can direct the circle to a particular target either by adjusting the pH or by taking advantage of natural variations in pH.

For example, two targets can be selected, a first target having many guanines and a second target with few guanines. A circular oligonucleotide can be prepared to include a first pair of cytosine-rich AP and P binding domains complementary to the first target and a second pair of cytosine-poor AP and P binding domains complementary to the second target in accordance with the procedures provided by the present invention. At low pH values, e.g. about pH 5.0 to 6.5, binding to the guanine-rich target is very highly favored whereas at high pH values, e.g. about pH 7.2 to 9.0, binding to the guanine-poor target is highly favored. Such oligonucleotides are therefore multifunctional, conformationally mobile ligands capable of controlled, selective binding to more than a single target site.

Moreover the selectivity of circular oligonucleotides can be controlled by taking advantage of pH variations in vivo as well as in vitro, since variations in pH occur naturally in vivo as well as being experimentally generated in vitro. For example, solid tumors can have a pH of 5.5 to 6.8 which is considerably lower than the average intracellular pH of 7.4 (Meyer et al. 1948 Cancer Res. 8: 513).

Therefore, according to the present invention, the biosynthesis of a DNA, an RNA or a protein within a targeted mammalian tumor can be selectively regulated, without substantially affecting the biosynthesis of DNA, RNA or proteins in non-targeted cells, e.g., that DNA, RNA or protein in a neighboring normal cell. This can be accomplished in accordance with the present invention by administering a circular oligonucleotide having a cytosine-rich pair of P and AP binding domains as well as a cytosine-poor pair of P and AP binding domains, wherein the cytosine-rich P and AP domains bind to the target within a nucleic acid template for the DNA, RNA or protein. Since the pH in such a solid tumor is lower than the pH of surrounding normal tissues, the circular oligonucleotide preferentially binds to the guanine-rich target within the tumor. However, in normal tissues where the pH is higher, the circular oligonucleotide has less preference for the guanine-rich target and binds to the guanine-poor target. By selecting a guanine-rich target whose function is essential for cell growth or survival, and a guanine-poor target with a non-essential function, the growth of the tumor can thereby be inhibited or arrested.

Unlike linear oligonucleotides, the present circular oligonucleotides can displace one strand of a double-stranded target under conditions where denaturation of the double-stranded target is thermodynamically unfavorable. Linear oligonucleotides do not have this capacity to displace a strand of a duplex. For example, the half-life of a double-stranded target in the presence of a complementary linear oligonucleotide is about 58 min, i.e. so long that the linear oligonucleotide has little utility for displacing one strand of the duplex target. However, a double-stranded target has a half-life of only 30 sec in the presence of the present circular oligonucleotides. Therefore, the circular oligonucleotides of the present invention have utility not only for binding single-stranded targets, but also for binding to double-stranded targets. Accordingly, since both single- and double-stranded nucleic acids are available as targets for the present circular oligonucleotides, these circular oligonucleotides can have greater utility than linear oligonucleotides. For example, the present circular oligonucleotides are better regulators of biological processes in vivo and better in vitro diagnostic probes than corresponding linear oligonucleotides.

When the nucleic acid template extends beyond the central triple-stranded target:circle complex, a P or an AP domain may bind as duplex on either side of the triple standard complex. Hence a target:circular oligonucleotide complex can be partially two stranded and partially three-stranded, wherein two-stranded portions can be P:target duplexes, without bound AP nucleotides, or AP:target duplexes, without bound P nucleotides. This binding arrangement is a staggered binding arrangement.

Each P domain, AP domain and target can independently have about 2 to about 200 nucleotides with preferred lengths being about 4 to about 100 nucleotides. The most preferred lengths are 6 to 36 nucleotides.

The P and AP domains are separated by loop domains which can independently have from about 2 to about 2000 nucleotides. A preferred loop length is from about 3 to about 8 nucleotides with an especially preferred length being about 5 nucleotides.

According to the present invention, the loop domains do not have to be composed of nucleotide bases. Non-nucleotide loops can make the present circular oligonucleotides cheaper to produce. More significantly, circular oligonucleotides with non-nucleotide loops are more resistant to nucleases and therefore have a longer biological half-life than linear oligonucleotides. Furthermore, loops having no charge, or a positive charge, can be used to promote binding by eliminating negative charge repulsions between the loop and target. In addition, circular oligonucleotides having uncharged or hydrophobic non-nucleotide loops can penetrate cellular membranes better than circular oligonucleotides with nucleotide loops.

As contemplated herein, non-nucleotide loop domains can be composed of alkyl chains, polyethylene glycol or oligoethylene glycol chains or other chains providing the necessary steric or flexibility properties which are compatible with oligonucleotide synthesis. The length of these chains is equivalent to about 2 to about 2000 nucleotides, with preferred lengths equivalent to about 3 to about 8 nucleotides. The most preferred length for these chains is equivalent to about 5 nucleotides.

Preferred chains for non-nucleotide loop domains are polyethylene glycol or oligoethylene glycol chains. In particular, oligoethylene glycol chains having a length similar to a 5 nucleotide chain, e.g. a pentaethylene glycol, a hexaethylene glycol or a heptaethylene glycol chain, are preferred.

The circular oligonucleotides are single-stranded DNA or RNA, with the bases guanine (G), adenine (A), thymine (T), cytosine (C) or uracil (U) in the nucleotides, or with any nucleotide analog that is capable of hydrogen bonding in a parallel or anti-parallel manner. Nucleotide analogs include pseudocytidine, isopseudocytidine, 3-aminophenyl-imidazole, 2'-O-methyladenosine, 7-deazadenosine, 7-deazaguanosine, 4-acetylcytidine, 5-(carboxy-hydroxylmethyl)-uridine, 2'-O-methylcytidine, 5-carboxymethylaminomethyl-2-thioridine, 5-carboxymethylamino-methyluridine, dihydrouridine, 2'-O-methyluridine, 2'-O-methyl-pseudouridine, beta,D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, 5-methyluridine, N6-methyl-adenosine, 7-methylguanosine, 5-methylaminomethyluridine, 5-methoxyaminomethyl-2-thiouridine, β-D-mannosylqueosine, 5-methoxycarbonylmethyluridine, 5-methoxyuridine, 2-methyl-thio-N6-isopentenyladenosine, N-(9-beta-D-ribofuranosyl-2-methylthiopurine-6-yl)carbamoyl)threonine, N-(9-beta-D-ribofuranosylpurine-6-yl)-N-methylcarbamoyl)threonine. When possible, either ribose or deoxyribose sugars can be used with these analogs. Nucleotides bases in an α-anomeric conformation can also be used in the circular oligonucleotides of the present invention.

Preferred nucleotide analogs have unmodified G, A, T, C and U bases; pyrimidine analogs with lower alkyl, lower alkoxy, lower alkylamine, phenyl or lower alkyl substituted phenyl groups in the 5 position of the base and purine analogs with similar groups in the 7 or 8 position of the base. Especially preferred nucleotide analogs are 5-methylcytosine, 5-methyluracil, diaminopurine, and nucleotides with a 2'-O-methyl-ribose moiety in place of ribose or deoxyribose. As used herein lower alkyl, lower alkoxy and lower alkylamine contain from 1 to 6 carbon atoms and can be straight chain or branched. These groups include methyl, ethyl, propyl, isopropyl, butyl, isobutyl, tertiary butyl, amyl, hexyl and the like. A preferred alkyl group is methyl.

Circular oligonucleotides can be made first as linear oligonucleotides and then circularized. Linear oligonucleotides can be made by any of a myriad of procedures known for making DNA or RNA oligonucleotides. For example, such procedures include enzymatic synthesis and chemical synthesis.

Enzymatic methods of DNA oligonucleotide synthesis frequently employ Klenow, T7, T4, Taq or *E. coli* DNA polymerases as described in Sambrook et al. Enzymatic methods of RNA oligonucleotide synthesis frequently employ SP6, T3 or T7 RNA polymerase as described in Sambrook et al. Reverse transcriptase can also be used to synthesize DNA from RNA (Sambrook et al.). To prepare oligonucleotides enzymatically requires a template nucleic acid which can either be synthesized chemically, or be obtained as mRNA, genomic DNA, cloned genomic DNA, cloned cDNA or other recombinant DNA. Some enzymatic methods of DNA oligonucleotide synthesis can require an additional primer oligonucleotide which can be synthesized chemically. Finally, linear oligonucleotides can be prepared by PCR techniques as described, for example, by Saiki et al., 1988, Science 239:487.

Chemical synthesis of linear oligonucleotides is well known in the art and can be achieved by solution or solid phase techniques. Moreover, linear oligonucleotides of defined sequence can be purchased commercially or can be made by any of several different synthetic procedures including the phosphoramidite, phosphite triester, H-phosphonate and phosphotriester methods, typically by automated synthesis methods. The synthesis method selected can depend on the length of the desired oligonucleotide and such choice is within the skill of the ordinary artisan. For example, the phosphoramidite and phosphite triester method produce oligonucleotides having 175 or more nucleotides while the H-phosphonate method works well for oligonucleotides of less than 100 nucleotides. If modified bases are incorporated into the oligonucleotide, and particularly if modified phosphodiester linkages are used, then the synthetic procedures are altered as needed according to known procedures. In this regard, Uhlmann et al. (1990, Chemical Reviews 90: 543–584) provide references and outline procedures for making oligonucleotides with modified bases and modified phosphodiester linkages.

Synthetic, linear oligonucleotides may be purified by polyacrylamide gel electrophoresis, or by any of a number of chromatographic methods, including gel chromatography and high pressure liquid chromatography. To confirm a nucleotide sequence, oligonucleotides may be subjected to DNA sequencing by any of the known procedures, including Maxam and Gilbert sequencing, Sanger sequencing, capillary electrophoresis sequencing the wandering spot sequencing procedure or by using selective chemical degradation of oligonucleotides bound to Hybond paper. Sequences of short oligonucleotides can also be analyzed by plasma desorption mass spectroscopy or by fast atom bombardment (McNeal, et al., 1982, J. Am. Chem. Soc. 104: 976; Viari, et al., 1987, Biomed. Environ. Mass Spectrom. 14:83; Grotjahn et al., 1982, Nuc. Acid Res. 10: 4671). Sequencing methods are also available for RNA oligonucleotides.

The present invention provides several methods of preparing circular oligonucleotides from linear precursors (i.e. precircles), including a method wherein a precircle is synthesized and bound to an end-joining-oligonucleotide and the two ends of the precircle are joined. Any method of joining two ends of an oligonucleotide is contemplated by the present invention, including chemical methods employing, for example, known coupling agents like BrCN, N-cyanoimidazole $ZnCl_2$, 1-ethyl-3-(3-dimethylaminopropyl)carbodiimide and other carbodiimides and carbonyl diimidazoles. Furthermore, the ends of a precircle can be joined by condensing a 5' phosphate and a 3' hydroxy, or a 5' hydroxy and a 3' phosphate.

Figure 2:
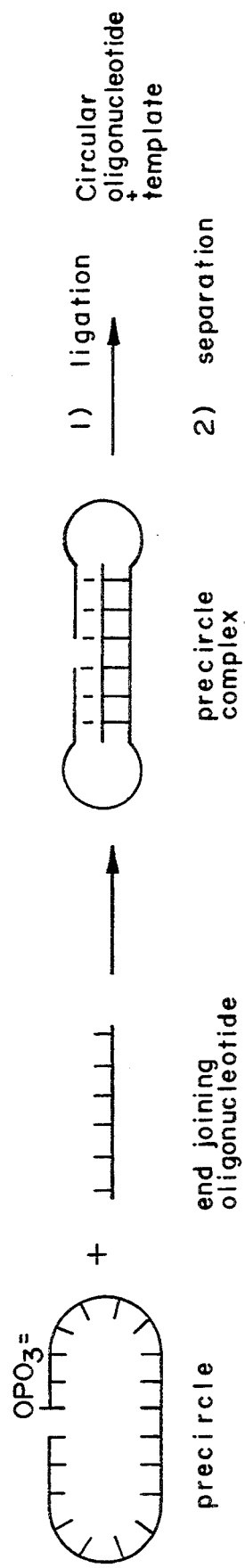
Figure 4:
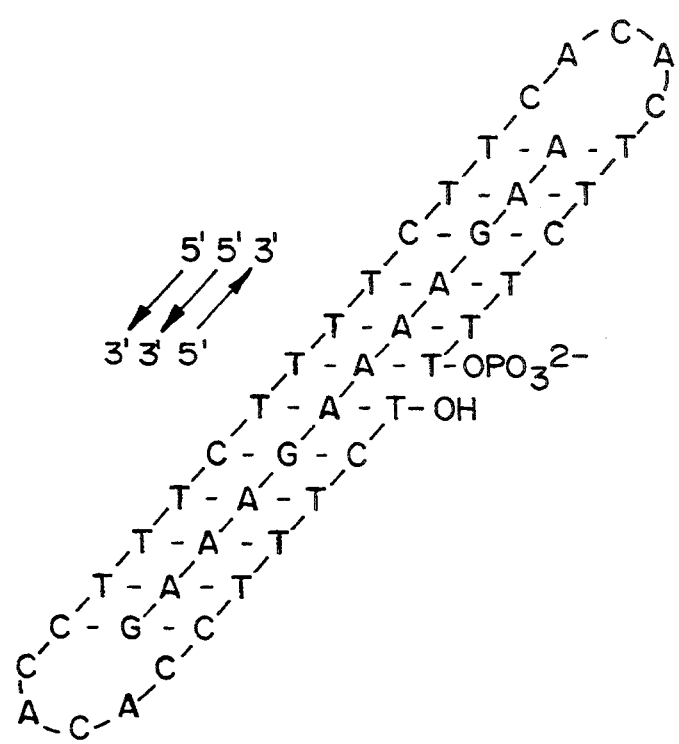

In accordance with the present invention, a simple one-step chemical method is provided to construct the subject circular oligonucleotides, or circles, from precircles. An oligonucleotide is constructed which has the same sequence as the target nucleic acid; this is the end-joining oligonucleotide. A DNA or RNA linear precircle is chemically or enzymatically synthesized and phosphorylated on its 5' or 3' end, again by either chemical or enzymatic means. The precircle and the end-joining oligonucleotide are mixed and annealed, thereby forming a complex in which the 5' and 3' ends of the precircle are adjacent, as depicted in FIG. 2. It is preferred that the ends of the precircle fall within a binding domain, not within a loop, and preferably within the anti-parallel binding domain rather than the parallel domain. Moreover, it is preferred that a precircle have a 3'-phosphate rather than a 5'-phosphate. After complex formation, the ends undergo a condensation reaction in a buffered aqueous solution containing divalent metal ions and BrCN at about pH 7.0. In a preferred embodiment the buffer is imidazole-Cl at pH 7.0 with a divalent metal such as Ni, Zn, Mn, or Co. Ni is the most preferred divalent metal. Condensation occurs after about 6–48 hr. of incubation at 4°–37° C. Other divalent metals, such as Cu, Pb, Ca and Mg, can also be used.

One method for RNA circularization incorporates the appropriate nucleotide sequences, preferably in a loop domain, into an RNA oligonucleotide to promote self splicing, since a circular product is formed under the appropriate conditions (Sugimoto et al., 1988, Biochemistry: 27: 6384–6392).

Enzymatic circle closure is also possible using DNA ligase or RNA ligase under conditions appropriate for these enzymes.

Circular oligonucleotides can be separated from the template by denaturing gel electrophoresis or melting followed by gel electrophoresis, size selective chromatography, or other appropriate chromatographic or electrophoretic methods. The recovered circular oligonucleotide can be further purified by standard techniques as needed for its use in the methods of the present invention.

The present invention also contemplates derivatization or chemical modification of the subject oligonucleotides with chemical groups to facilitate cellular uptake. For example, covalent linkage of a cholesterol moiety to an oligonucleotide can improve cellular uptake by 5- to 10- fold which in turn improves DNA binding by about 10- fold (Boutorin et al., 1989, FEBS Letters 254: 129–132). Other ligands for cellular receptors may also have utility for improving cellular uptake, including, e.g. insulin, transferrin and others. Similarly, derivatization of oligonucleotides with poly-L-lysine can aid oligonucleotide uptake by cells (Schell, 1974, Biochem. Biophys. Acta 340: 323, and Lemaitre et al., 1987, Proc. Natl. Acad. Sci. USA 84:648). Certain protein carriers can also facilitate cellular uptake of oligonucleotides, including, for example, serum albumin, nuclear proteins possessing signals for transport to the nucleus, and viral or bacterial proteins capable of cell membrane penetration. Therefore, protein carriers are useful when associated with or linked to the circular oligonucleotides of this invention. Accordingly, the present invention contemplates derivatization of the subject circular oligonucleotides with groups capable of facilitating cellular uptake, including hydrocarbons and non-polar groups, cholesterol, poly-L-lysine and proteins, as well as other aryl or steroid groups and polycations having analogous beneficial effects, such as phenyl or naphthyl groups, quinoline, anthracene or phenanthracene groups, fatty acids, fatty alcohols and sesquiterpenes, diterpenes and steroids.

The present invention further contemplates derivatization of the subject oligonucleotides with agents that can cleave or modify the target nucleic acid or other nucleic acid strands associated with or in the vicinity of the target. For example, viral DNA or RNA can be targeted for destruction without harming cellular nucleic acids by administering a circular oligonucleotide complementary to the targeted nucleic acid which is linked to an agent that, upon binding, can cut or render the viral DNA or RNA inactive. Nucleic acid destroying agents that are contemplated by the present invention as having cleavage or modifying activities include, for example, RNA and DNA nucleases, ribozymes that can cleave RNA, azidoproflavine, acridine, EDTA/Fe, chloroethylamine, azidophenacyl and phenanthroline/Cu. Uhlmann et al. (1990, Chemical Reviews 90: 543–584) provide further information on the use of such agents and methods of derivatizing oligonucleotides that can be adapted for use with the subject circular oligonucleotides.

Derivatization of the subject circular oligonucleotides with groups that facilitate cellular uptake or target binding, as well as derivatization with nucleic acid destroying agents or drugs, can be done by any of the procedures known to one skilled in the art. Moreover, the desired groups can be added to nucleotides before synthesis of the oligonucleotide. For example, these groups can be linked to the 5-position of T or C and these modified T and C nucleotides can be used for synthesis of the present circular oligonucleotides. In addition, derivatization of selected nucleotides permits incorporation of the group into selected domains of the circular oligonucleotide. For example, in some instances it is preferable to incorporate certain groups into a loop where that group will not interfere with binding, or into an AP or P domain to facilitate cleavage or modification of the target nucleic acid.

In accordance with the present invention, modification in the phosphodiester backbone of circular oligonucleotides is also contemplated. Such modifications can aid uptake of the oligonucleotide by cells or can extend the biological half-life of such nucleotides. For example, circular oligonucleotides may penetrate the cell membrane more readily if the negative charge on the internucleotide phosphate is eliminated. This can be done by replacing the negatively charged phosphate oxygen with a methyl group, an amine or by changing the phosphodiester linkage into a phosphotriester linkage by addition of an alkyl group to the negatively charged phosphate oxygen. Alternatively, one or more of the phosphate atoms which is part of the normal phosphodiester linkage can be replaced. For example, NH-P, $CH_2$-P or S-P linkages can be formed. Accordingly, the present invention contemplates using methylphosphonates, phosphorothioates, phosphorodithioates, phosphotriesters and phosphorusboron (Sood et al., 1990, J. Am. Chem. Soc. 112: 9000) linkages. The phosphodiester group can be replaced with siloxane, carbonate, acetamidate or thioether groups. These modifications can also increase the resistance of the subject oligonucleotides to nucleases. Methods for synthesis of oligonucleotides with modified phosphodiester linkages are reviewed by Uhlmann et al.

Circular oligonucleotides with non-nucleotide loops can be prepared by any known procedure. For example, Durand et al. (1990, Nucleic Acids Res. 18:6353–6359) provides synthetic procedures for linking non-nucleotide chains to DNA. Such procedures can generally be adapted to permit an automated synthesis of a linear oligonucleotide precursor which is then used to make a circular oligonucleotide of the present invention. In general, groups reactive with nucleotides in standard DNA synthesis, e.g. phosphoramidite, H-phosphonate, dimethoxytrityl, monomethoxytrityl and the like, can be placed at the ends of non-nucleotide chains and nucleotides corresponding to the ends of P and AP domains can be linked thereto.

Additionally, different nucleotide sugars can be incorporated into the oligonucleotides of this invention. For example, RNA oligonucleotides can be used since RNA:DNA hybrids are more stable than DNA:DNA hybrids. Additional binding stability can also be provided by using 2'-O-methyl ribose in the present circular oligonucleotides. Phosphoramidite chemistry can be used to synthesize RNA oligonucleotides as described (Reese, C. B. In *Nucleic Acids & Molecular Biology*; Springer-Verlag: Berlin, 1989; Vol. 3, p. 164; and Rao, et al., 1987, Tetrahedron Lett. 28: 4897).

The synthesis of RNA 2'-O-methyloligoribonucleotides and DNA oligonucleotides differ only slightly. RNA 2'-O-methyloligonucleotides can be prepared with minor modifications of the amidite, H-phosphonate or phosphotriester methods (Shibahara et al, 1987, Nucleic Acids Res. 15: 4403; Shibahara et al., 1989, Nucleic Acids Res. 17: 239; Anoue et al., 1987, Nucleic Acids Res. 15: 6131).

In another embodiment the present invention, circular oligonucleotides can accelerate the dissociation of a double-stranded nucleic acid target. Therefore the double-stranded nucleic acid target does not have to be subjected to denaturing conditions before binding of the present circular oligonucleotides. Thus, the circular oligonucleotides can bind to both single- and double-stranded nucleic acid targets under a wider variety of conditions, and particularly under physiological conditions. The present circular oligonucleotides are several orders of magnitude faster at accelerating duplex nucleic acid strand displacement than are the corresponding linear oligonucleotides.

The present invention therefore provides a means to displace one strand of a double-stranded nucleic acid target with one of the subject circular oligonucleotides without the necessity of prior denaturation of the double-stranded nucleic acid target. Thus, the present invention provides a method of strand displacement in a double-stranded nucleic acid target by contacting the target with one of the subject circular oligonucleotides for a time and under conditions effective to denature said target and permit the circular oligonucleotide to bind to the target. The target for the present circular oligonucleotides can be a double-stranded nucleic acid, either RNA or DNA, which has not undergone denaturation by, for example, heating or exposure to alkaline pH.

As used herein, the nucleic acids for strand displacement can be present in an organism or present in a sample which includes an impure or pure nucleic acid preparation, a tissue section, a prokaryotic or eukaryotic cell smear, a chromosomal squash and the like. Moreover, the nucleic acid targets for strand displacement by the present circular oligonucleotides include viral, bacterial, fungal or mammalian nucleic acids.

According to the present invention, conditions effective to denature the target by strand displacement and thereby permit binding, include having a suitable circular oligonucleotide to target nucleic acid ratio. Moreover, as used herein a suitable ratio of circular oligonucleotide to target is about 1 to about 100, and is preferably about 1 to about 50.

Moreover, as used herein a time effective to denature a double-stranded nucleic acid by strand-displacement with an oligonucleotide of the present invention is about 1 minute to about 16 hours.

A circular oligonucleotide can associate with a duplex target by first binding in the P domain. Such P domain binding juxtaposes the AP domain nucleotides to compete for Watson-Crick binding to target nucleotide. This P domain pre-association followed by AP domain nucleotide competition for Watson-Crick binding may form the basis for the observed acceleration in strand displacement by circular oligonucleotides.

In summary, the subject circular oligonucleotides have three important features which enable duplex strand displacement. First, the circular oligonucleotide has the ability to preassociate, e.g. by binding of a P domain to the target, which results in a high local concentration of P, AP and target. Second, the circular oligonucleotide contains a second (i.e., AP), binding domain, which competes for binding to a complementary strand of the duplex. Finally, the circular oligonucleotide binds with higher affinity than the displaced strand of the duplex, thereby driving the reaction to completion.

The present invention contemplates a variety of utilities for the subject circular oligonucleotides which are made possible by their selective and stable binding properties with both single- and double-stranded targets. Some utilities include, but are not limited to: use of circular oligonucleotides of defined sequence, bound to a solid support, for affinity isolation of complementary nucleic acids; use of the subject oligonucleotides to provide sequence specific stop signals during polymerase chain reaction (PCR); covalent attachment of a drug, drug analog or other therapeutic agent to circular oligonucleotides to allow cell type specific drug delivery; labeling circular oligonucleotides with a detectable reporter molecule for localizing, quantitating or identifying complementary target nucleic acids; and binding circular oligonucleotides to a cellular or viral nucleic acid template and regulating biosynthesis directed by that template.

The subject circular oligonucleotides can be attached to a solid support such as silica, cellulose, nylon, and other natural or synthetic materials that are used to make beads, filters, and column chromatography resins. Attachment procedures for nucleic acids to solid supports of these types are well known; any known attachment procedure is contemplated by the present invention. A circular oligonucleotide attached to a solid support can then be used to isolate a complementary nucleic acid. Isolation of the complementary nucleic acid can be done by incorporating the oligonucleotide:solid support into a column for chromatographic procedures. Other isolation methods can be done without incorporation of the oligonucleotide:solid support into a column, e.g. by utilization of filtration procedures. Circular oligonucleotide:solid supports can be used, for example, to isolate poly(A)+ mRNA from total cellular or viral RNA by making a circular oligonucleotide with P and AP domain poly(dT) or poly(U) sequences. Circular oligonucleotides are ideally suited to applications of this type because they are nuclease resistant and bind target nucleic acids so strongly.

Further utilities are available for the subject oligonucleotides in the field of polymerase chain reaction (PCR) technology. PCR technology provides methods of synthesizing a double-standard DNA fragment encoded in a nucleic acid template between two known nucleic acid sequences which are employed as primer binding sites. In some instances it is desirable to produce a single-stranded DNA fragment before or after having made some of the double stranded fragment. This can be done by, for example, binding a circular oligonucleotide of the present invention to one of the primer binding sites or to a site lying between the primer binding sites.

The present invention also contemplates using the subject circular oligonucleotides for targeting drugs to specific cell types. Such targeting can allow selective destruction or enhancement of particular cell types, e.g. inhibition of tumor cell growth can be attained. Different cell types express different genes, so that the concentration of a particular mRNA can be greater in one cell type relative to another cell type, such an mRNA is a target mRNA for cell type specific drug delivery by circular oligonucleotides linked to drugs or drug analogs. Cells with high concentrations of target mRNA are targeted for drug delivery by administering to the cell a circular oligonucleotide with a covalently linked drug that is complementary to the target mRNA.

The present invention also contemplates labeling the subject circular oligonucleotides for use as probes to detect a target nucleic acid. Labelled circular oligonucleotide probes have utility in diagnostic and analytical hybridization procedures for localizing, quantitating or detecting a target nucleic acid in tissues, chromosomes or in mixtures of nucleic acids. Circular oligonucleotide probes of this invention represent a substantial improvement over linear nucleic acid probes because the circular oligonucleotides can replace one strand of a double-stranded nucleic acid, and because the present oligonucleotides have two binding domains which not only provide increased binding stability but also impart a greater sequence selectivity (or specificity) for the target:oligonucleotide interaction.

Labeling of a circular oligonucleotide can be done by incorporating nucleotides linked to a "reporter molecule" into the subject circular oligonucleotides. A "reporter molecule", as defined herein, is a molecule or atom which, by its chemical nature, provides an identifiable signal allowing detection of the circular oligonucleotide. Detection can be either qualitative or quantitative. The present invention contemplates using any commonly used reporter molecule including radionuclides, enzymes, biotins, psoralens, fluorophores, chelated heavy metals, and luciferin. The most commonly used reporter molecules are either enzymes, fluorophores or radionuclides linked to the nucleotides which are used in circular oligonucleotide synthesis. Commonly used enzymes include horseradish peroxidase, alkaline phosphatase, glucose oxidase and $\beta$-galactosidase, among others. The substrates to be used with the specific enzymes are generally chosen because a detectably colored product is formed by the enzyme acting upon the substrate. For example, p-nitrophenyl phosphate is suitable for use with alkaline phosphatase conjugates; for horseradish peroxidase, 1,2-phenylenediamine, 5-aminosalicyclic acid or toluidine are commonly used. The probes so generated have utility in the detection of a specific DNA or RNA target in, for example, Southern analysis, Northern analysis, in situ hybridization to tissue sections or chromosomal squashes and other analytical and diagnostic procedures. The methods of using such hybridization probes are well known and some examples of such methodology are provided by Sambrook et al.

The present circular oligonucleotides can be used in conjunction with any known detection or diagnostic procedure which is based upon hybridization of a probe to a target nucleic acid. Moreover, the present circular oligonucleotides can be used in any hybridization procedure which quantitates a target nucleic acid, e.g., by competitive hybridization between a target nucleic acid present in a sample and a labeled tracer target for one of the present oligonucleotides. Furthermore, the reagents needed for making a circular oligonucleotide probe and for utilizing such a probe in a hybridization procedure can be marketed in a kit.

The kit can be compartmentalized for ease of utility and can contain at least one first container providing reagents for making a precircle precursor for a circular oligonucleotide, at least one second container providing reagents for labeling the precircle with a reporter molecule, at least one third container providing regents for circularizing the precircle, and at least one fourth container providing reagents for isolating the labeled circular oligonucleotide.

Moreover the present invention provides a kit for isolation of a template nucleic acid. Such a kit has at least one first container providing a circular oligonucleotide which is complementary to a target contained within the template. For example, the template nucleic acid can be cellular and/or viral Poly(A)+ mRNA and the target can be the poly(A)+ tail. Hence circular oligonucleotides of the present invention which have utility for isolation of poly(A)+ mRNA have P and AP domain sequences of poly(dT) or poly(U).

For use in a kit for the detection of any target nucleic acid, the circular oligonucleotides of the present invention can be linked to a reporter molecule and additional containers providing reagents for linking the reporter molecule to the circular oligonucleotide or for detecting a linked reporter molecule can also be provided in the kit.

Furthermore, the present invention provides kits useful when diagnosis of a disease depends upon detection of a specific, known target nucleic acid. Such nucleic acid targets can be, for example, a viral nucleic acid, an extra or missing chromosome or gene, a mutant cellular gene or chromosome, an aberrantly expressed RNA and others. The kits can be compartmentalized to contain at least one first container providing a circular oligonucleotide linked to a reporter molecule and at least one second container providing reagents for detection of the reporter molecule.

Therefore, as contemplated by the present invention, the kits disclosed herein can include any elements recognized or conventionally used by the skilled artisan for constructing, purifying and using oligonucleotides. Moreover, the present kits can include specific chemical reagents or end-joining-oligonucleotides for making the present circular oligonucleotide.

One aspect of the present invention provides a method of regulating biosynthesis of a DNA, an RNA or a protein by contacting at least one of the subject circular oligonucleotides with a nucleic acid template for that DNA, that RNA or that protein in an amount and under conditions sufficient to permit the binding of the oligonucleotide(s) to a target sequence contained in the template. The binding between the oligonucleotide(s) and the target blocks access to the template, and thereby regulates biosynthesis of the nucleic acid or the protein. Blocking access to the template prevents proteins and nucleic acids involved in the biosynthetic process from binding to the template, from moving along the template, or from recognizing signals encoded within the template. Alternatively, when the template is RNA, regulation can be accomplished by allowing selective degradation of the template. For example, RNA templates bound by the subject circular oligonucleotides are susceptible to degradation by RNase H and RNase H degradation of a selected RNA template can thereby regulate use of the template in biosynthetic processes.

As used herein, biosynthesis of a nucleic acid or a protein includes cellular and viral processes such as DNA replication, DNA reverse transcription, RNA transcription, RNA splicing, RNA polyadenylation, RNA translocation and protein translation, and of which can lead to production of DNA, RNA or protein, and involve a nucleic acid template at some stage of the biosynthetic process.

As used herein, regulating biosynthesis includes inhibiting, stopping, increasing, accelerating or delaying biosynthesis. Regulation may be direct or indirect, i.e. biosynthesis of a DNA, RNA or protein may be regulated directly by binding a circular oligonucleotide to the template for that DNA, RNA or protein; alternatively, biosynthesis may be regulated indirectly by oligonucleotide binding to a second template encoding a protein that plays a role in regulating the biosynthesis of the first DNA, RNA or protein.

The nucleic acid templates can be RNA or DNA and can be single-stranded or double-stranded. While the present circular oligonucleotides bind to only one strand of a target present in the template, double-stranded templates are opened during biosynthetic processes and thereby become available for binding. Furthermore, the P domain of the present circular oligonucleotides can bind to a double-stranded target and place AP domain nucleotides in a position to compete for Watson-Crick binding to target nucleotides.

DNA replication from a DNA template is mediated by proteins which bind to an origin of replication where they open the DNA and initiate DNA synthesis along the DNA template. To inhibit DNA replication in accordance with the present invention, circular oligonucleotides are selected which bind to one or more targets in an origin of replication. Such binding blocks template access to proteins involved in DNA replication. Therefore initiation and procession of DNA replication is inhibited. As an alternative method of inhibiting DNA replication, expression of the proteins which mediate DNA replication can be inhibited at, for example, the transcriptional or translational level. As one skilled in the art recognizes, DNA replication can also be increased, e.g. by inhibiting expression of a protein repressor of DNA replication.

DNA replication from an RNA template is mediated by reverse transcriptase binding to a region of RNA also bound by a nucleic acid primer. To inhibit DNA replication from an RNA template, reverse transcriptase or primer binding can be blocked by binding a circular oligonucleotide to the-primer binding site, and thereby blocking access to that site. Moreover, inhibition of DNA replication can occur by binding a circular oligonucleotide to a site residing in the RNA template since such binding can block access to that site and to downstream sites, i.e. sites on the 3' side of the target site.

To initiate RNA transcription, RNA polymerase recognizes and binds to specific start sequences, or promoters, on a DNA template. Binding of RNA polymerase opens the DNA template. There are also additional transcriptional regulatory elements that play a role in transcription and are located on the DNA template. These transcriptional regulatory elements include enhancer sequences, upstream activating sequences, repressor binding sites and others. All such promoter and transcriptional regulatory elements, singly or in combination, are targets for the subject circular oligonucleotides. Oligonucleotide binding to these sites can block RNA polymerase and transcription factors from gaining access to the template and thereby regulating, e.g., increasing or decreasing, the production of RNA, especially mRNA and tRNA. Additionally, the subject oligonucleotides can be targeted to the coding region or 3'-untranslated region of the DNA template to cause premature termination of transcription. One skilled in the art can readily design oligonucleotides for the above target sequences from the known sequence of these regulatory elements, from coding region sequences, and from consensus sequences.

RNA transcription can be increased by, for example, binding a circular oligonucleotide to a negative transcriptional regulatory element or by inhibiting biosynthesis of a protein that can repress transcription. Negative transcriptional regulatory elements include repressor sites or operator sites, wherein a repressor protein binds and blocks transcription. Oligonucleotide binding to repressor or operator sites can block access of repressor proteins to their binding sites and thereby increase transcription.

The primary RNA transcript made in eukaryotic cells, or pre-mRNA, is subject to a number of maturation processes before being translocated into the cytoplasm for protein translation. In the nucleus, introns are removed from the pre-mRNA in splicing reactions. The 5' end of the mRNA is modified to form the 5' cap structure, thereby stabilizing the mRNA. Various bases are also altered. The polyadenylation of the mRNA at the 3' end is thought to be linked with export from the nucleus. The subject circular oligonucleotides can be used to block any of these processes.

A pre-mRNA template is spliced in the nucleus by ribonucleoproteins which bind to splice junctions and intron branch point sequences in the pre-mRNA. Consensus sequences for 5' and 3' splice junctions and for the intron branch point are known. For example, inhibition of ribonucleoprotein binding to the splice junctions or inhibition of covalent linkage of the 5' end of the intron to the intron branch point can block splicing. Maturation of a pre-mRNA template can, therefore, be blocked by preventing access to these sites, i.e. by binding circular oligonucleotides of this invention to a 5' splice junction, an intron branch point or a 3' splice junction. Splicing of a specific pre-mRNA template can be inhibited by using circular oligonucleotides with sequences that are complementary to the specific pre-mRNA splice junction(s) or intron branch point. In a further embodiment, a collection of related splicing of pre-mRNA templates can be inhibited by using a mixture of circular oligonucleotides having a variety of sequences that, taken together, are complementary to the desired group of splice junction and intron branch point sequences.

Polyadenylation involves recognition and cleavage of a pre-mRNA by a specific RNA endonuclease at specific polyadenylation sites, followed by addition of a poly(A) tail onto the 3' end of the pre-mRNA. Hence, any of these steps can be inhibited by binding the subject oligonucleotides to the appropriate site.

RNA translocation from the nucleus to the cytoplasm of eukaryotic cells appears to require a poly(A) tail. Thus, a circular oligonucleotide is designed in accordance with this invention to bind to the poly(A) tail and thereby block access to the poly (A) tail and inhibit RNA translocation. For such an oligonucleotide, both the P and AP domains can consist of about 10 to about 50 thymine residues, and preferably about 20 residues. Especially preferred P and AP domain lengths for such an oligonucleotide are about 6 to about 12 thymine residues.

Protein biosynthesis begins with the binding of ribosomes to an mRNA template, followed by initiation and elongation of the amino acid chain via translational "reading" of the mRNA. Protein biosynthesis, or translation, can thus be blocked or inhibited by blocking access to the template using the subject circular oligonucleotides to bind to targets in the template mRNA. Such targets contemplated by this invention include the ribosome binding site (Shine-Delgarno sequence), the 5' mRNA cap site, the initiation codon, and sites in the protein coding sequence. There are also classes of protein which share domains of nucleotide sequence homology. Thus, inhibition of protein biosynthesis for such a class can be accomplished by targeting the homologous protein domains (via the coding sequence) with the subject circular oligonucleotides.

Regulation of biosynthesis by any of the aforementioned procedures has utility for many applications. For example, genetic disorders can be corrected by inhibiting the production of mutant or over-produced proteins, or by increasing production of under-expressed proteins; the expression of genes encoding factors that regulate cell proliferation can be inhibited to control the spread of cancer; and virally encoded functions can be inhibited to combat viral infection.

In accordance with the present invention, it has been determined that in some instances the biosynthesis of a DNA, RNA or protein is more effectively regulated by binding the template at more than one target site. The present circular oligonucleotides which are prepared to bind to multiple target sites, e.g. by having more than one P or AP domain, can also be more effective at regulating the biosynthesis of a DNA, RNA or protein than oligonucleotides which can bind only one target site. For example, the binding of two sites within a gene can provide greater inhibition than achieved with single-site binding (Maher et al. 1987 J. Arch. Biochem. Biophys. 253: 214–220; Tannock, I. F. in "The Basic Science of Oncology" 2nd ed.; Tannock, I. F. and Hill, R. P., eds. McGraw-Hill, New York, 348–349). In targeting viral sequences, the binding of two genes in a virus can inhibit viral replication more effectively than binding a single target. It has been shown, for example, that the use of multiple probes against a virus reduces the ability of the virus to escape inhibition by mutation (Kern et al. 1991 Science 252: 1708–1711). A broader spectrum of inhibition by targeting two mutants of one virus or two viruses which are commonly found together, such as HIV-1 and cytomegalovirus (CMV) can also be achieved in accordance with the present invention.

Therefore, the present methods of regulating the biosynthesis of a DNA, RNA or protein can also include binding to more than one target within a template, whether the targets are bound by separate circular oligonucleotides or by the same oligonucleotide which includes multiple P or multiple AP domains.

Some types of genetic disorders that can be treated by the circular oligonucleotides of the present invention include Alzheimer's disease, some types of arthritis, sickle cell anemia and others. Many types of viral infections can be treated by utilizing the circular oligonucleotides of the present invention, including infections caused by influenza, rhinovirus, HIV, herpes simplex, papilloma virus, cytomegalovirus, Epstein-Barr virus, adenovirus, vesticular stomatitus virus, rotavirus and respiratory syncytial virus among others. According to the present invention, animal and plant viral infections may also be treated by administering the subject oligonucleotides.

The c-myc gene is one example of a gene which can have a role in cell proliferation. Inhibition of c-myc expression has been demonstrated in vitro using a linear oligonucleotide complementary to a target 115 bp upstream of the c-myc transcription start site (Cooney et al., 1988, Science 241: 456–459). Circular oligonucleotides of SEQ ID NO:1, and SEQ ID NO:2, as depicted below, are complementary to the c-myc promoter at nucleotides $-131$ to $-120$ and $-75$ to $-62$, respectively, and are provided to inhibit c-myc expression in accordance with the present invention. As used in these depictions of SEQ ID NO:1 and SEQ ID NO:2, N can be any nucleotide or nucleotide analog.

SEQ ID NO:1

```
    1
  N C T C C C C G C C C T C N
 N                           N
N                             N
 N                           N
  N C T C C C C A C C C T C N
```

SEQ ID NO:2

```
    1
  N T C T T T T T T C T T T T C N
 N                               N
N                                 N
 N                               N
  N T C T T T T T T C T T T T C N
```

Human immunodeficiency virus (HIV) is a retrovirus causing acquired immunodeficiency syndrome (AIDS). The circular oligonucleotides of this invention provide a means of blocking the replication of the virus without deleteriously affecting normal cellular replication in humans infected with HIV. The retroviral genome is transcribed as a single, long transcript, part of which is spliced to yield RNA encoding viral envelope proteins. Inhibition of HIV infection can be accomplished by designing oligonucleotides to bind to a number of regions within the HIV genome, including coding regions for functions that replicate the genome (i.e., the pol or reverse transcriptase function) or functions that control gene expression (e.g. the tat, rev or other functions). However, previous work with linear oligonucleotides has suggested that splice sites, poly(A) addition signals, cap or initiator codon sites, and sites implicated in ribosome assembly can be particularly effective for inhibiting eucaryotic protein expression. Furthermore, the terminal structures of the retroviral genome are also excellent targets for inhibiting retrovirus production not only because these structures encode control regions which mediate the rate of transcription and replication, but also because these structures are repeated, allowing an oligonucleotide to bind and block access to each repeat.

Accordingly, the present invention provides two circular oligonucleotides, set forth in SEQ ID NO:3 and SEQ ID NO:4 wherein N is any nucleotide or nucleotide analog and Y is a pyrimidine or a pyrimidine analog. SEQ ID NO:3 is complementary to an HIV-1 splice junction (nucleotides 6039-52), while SEQ ID NO:4 is complementary to part of the tat gene (nucleotides 5974–88). The circular form of SEQ ID NO:3 is depicted below, wherein nucleotide number 1 is the first nucleotide in the P domain, i.e., the first T on the top line corresponds to base 1.

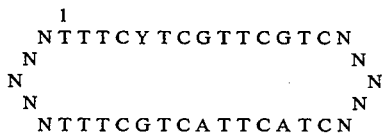

The circular form of SEQ ID NO:4 is depicted below wherein nucleotide number 1 is the first nucleotide of the P domain.

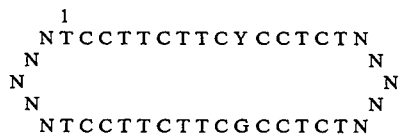

Circular oligonucleotides of SEQ ID NO:3 and SEQ ID NO:4 can inhibit HIV infection both in vitro and in vivo. In vitro screening for circular oligonucleotide effectiveness against HIV infection permits one skilled in the art to judge the stability of oligonucleotide: target binding and to assess in vivo efficacy and binding stability. To observe in vitro inhibition circular oligonucleotides can be added to the growth medium of an appropriate cell line infected with HIV. Cells can be pretreated with the circular oligonucleotides or circular oligonucleotides can be added at the time of infection or after HIV infection. Addition before or after infection allows assessment of whether the subject oligonucleotide can prevent or simply inhibit HIV infection respectively.

The extent of inhibition of HIV infection or replication can be judged by any of several assay systems, including assessment of the proportion of oligonucleotide-treated cells surviving after infection relative to survival of untreated cells, assessment of the number of syncytia formed in treated and untreated HIV infected cells and determination of the amount of viral antigen produced in treated and untreated cells.

In vivo studies of the efficacy of circular oligonucleotides can be done in a suitable animal host, such as transgenic mice, or chimpanzees. Levels of HIV antigens can be monitored to assess the effect of circular oligonucleotides on HIV replication and thereby to follow the course of the disease state. Alternatively, human volunteers with AIDS or ARC can be administered with the subject circular oligonucleotides since the oligonucleotides do not appear to be cytotoxic. The disease status of these volunteers can then be assessed to determine the efficacy of the subject oligonucleotides in treating and preventing AIDS infection.

A further aspect of this invention provides pharmaceutical compositions containing the subject circular oligonucleotides with a pharmaceutically acceptable carrier. In particular, the subject oligonucleotides are provided in a therapeutically effective amount of about 0.1 μg to about 100 mg per kg of body weight per day, and preferably of about 0.1 μg to about 10 mg per kg of body weight per day, to bind to a nucleic acid in accordance with the methods of this invention. Dosages can be readily determined by one of ordinary skill in the art and formulated into the subject pharmaceutical compositions.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The subject oligonucleotides may be administered topically or parenterally by, for example, by osmotic pump, intraveneous, intramuscular, intraperitoneal subcutaneous or intradermal route, or when suitably protected, the subject oligonucleotides may be orally administered. The subject oligonucleotides may be incorporated into a cream, solution or suspension for topical administration. For oral administration, oligonucleotides may be protected by enclosure in a gelatin capsule. Oligonucleotides may be incorporated into liposomes or lipsomes modified with polyethylene glycol for parenteral administration. Incorporation of additional substances into the liposome, for example, antibodies reactive against membrane proteins found on specific target cells, can help target the oligonucleotides to specific cell types.

Moreover, the present invention contemplates administering the subject circular oligonucleotides with an osmotic pump providing continuous infusion of such oligonucleotides, for example, as described in Rataiczak et al. (1992 Proc. Natl. Acad. Sci. USA 89: 11823–11827). Such osmotic pumps are commercially available, e.g., from Alzet Inc (Palo Alto, Calif.).

Topical administration and parenteral administration in a liposomal carrier is preferred.

The following examples further illustrate the invention.

EXAMPLE 1

Circularization of Oligonucleotides using an End Joining Oligonucleotide

According to the present invention, a simple one-step chemical method has been developed to construct circles from linear precursors (precircles). A DNA oligonucleotide was constructed which had the same sequence as the eventual target, this is the end-joining-oligonucleotide. A precircle oligonucleotide was then constructed and chemically phosphorylated on the 5'-end or 3'-end. As depicted in FIG. 2, the precircle and end-joining-oligonucleotide were mixed and allowed to form a complex in which the ends were adjacent. Cyanogen bromide, imidazole buffer, and a divalent metal were added. After incubation for 6–48 hr, the mixture was dialyzed, lyophilized, and the products were separated by denaturing 20% polyacrylamide gel electrophoresis. UV shadowing revealed major bands which comigrated with the precircle and the end-joining-oligonucleotide, along with one new product which migrated slightly more slowly than the precircle. No product was observed without added end-joining-oligonucleotide or in the absence of a 5'- or 3'-phosphate group on the precircle. The major bands were excised and eluted from the gel, dialyzed to remove salts and quantitated by absorbance at 260 nm. For reactions with precircles 1 and 2 (SEQ ID NO: 5 and SEQ ID NO: 6, respectively), using end-joining-oligonucleotides 4 and 5 (SEQ ID NO: 8 and SEQ ID NO: 9, respectively), the circles 6 and 7 were obtained in 40% and 58% yields, respectively. The sequences of each of these molecules and other oligonucleotides are depicted in FIG. 3.

The circular structure of products 6 and 7 was confirmed by resistance to 3' exonuclease digestion and to 5' dephosphorylation under reaction conditions in which a linear precircle was completely destroyed or dephosphorylated. Accordingly, the 3' exonuclease activity of T4 DNA polymerase cleaved linear precircles 1 and 2, but not circles 6 and 7. The linear precircles were also 5'-end labeled with $^{32}$p and then circularized. After reaction, the circular products were inert to calf alkaline phosphatase whereas the precircles completely released labeled $^{32}$p. The slightly slower gel mobility of the circles relative to the precircles was consistent with the occurrence of circularization.

Optimal Circularization Conditions

Many parameters were optimized to increase yields of the circular product, including oligonucleotide and precircle concentrations, temperature, reaction time, metal, metal concentration, BrCN concentration and pH. Improved circularization conditions provided an at least two-fold higher yield of circles compared to prior art conditions wherein two single-stranded oligonucleotides were joined (Luebke et al., 1989, J. Am. Chem. Soc. 111:8733 and Kanaya et al., 1986, Biochemistry 25: 7423). These improved conditions were:
  50 μM precircle
  55 μM end-joining-oligonucleotide
  100 mM NiCl
  200 mM imidazole HCl (pH 7.0)
  125 mM BrCN
  25° C., 36 hr.

However circle closure was also effective under the following conditions:
  3–200 μM precircle
  3–200 μM end-joining-oligonucleotide
  10–500 mM NiCl$_2$
  50–500 mM imidazole-HCl
  20–200 mM BrCN
  4°–37° C., 6–48 hr.

Other metals ($Zn^{2+}$, $Mn^{2+}$, $Co^{2+}$, $Cu^{2+}$, $Pb^{2+}$, $Ca^{2+}$, $Mg^{2+}$) also work in place of $Ni^{2+}$. Additionally the reaction is pH sensitive.

Closure in AP and P Domains

Closure of a circle in the AP domain was superior to closure in the P domain. Comparison of the circularization of precircles 2 and 3 (SEQ ID NO: 6 and SEQ ID NO: 7, respectively) around the same end-joining-oligonucleotide (i.e. 5,1SEQ ID NO: 9) indicated that circle 7 (having SEQ ID NO: 6) was formed with a 58% yield when closed in the AP domain (i.e. using precircle 2) and only a 35% yield when closed in the P domain (i.e. using precircle 3).

Condensing Reagents

Two reagents have been commonly used for chemical ligation of DNA and RNA, BrCN/imidazole/NiCl$_2$ and 1-ethyl-3-(3-dimethylaminopropyl)carbodiimide (EDC) (Kanaya et al. 1986 Biochemistry 25:7423 and Ashley et al. 1991 Biochemistry 30: 2927). Therefore, these reagents were were directly compared for efficacy in ligating a precircle to circular oligonucleotide 6 (FIG. 3 and SEQ ID NO: 5) using a dA$_{12}$ (SEQ ID NO: 8) end-joining-oligonucleotide.

BrCN/imidazole/NiCl$_2$ was used under the established optimal conditions except that ligation efficiency was observed at both 4° C. and 25° C. EDC was used at 200 mM with 20 mM MgCl$_2$, 50 mM MES (pH 6.0) at 4° C. or 25° C. with incubation for 4 days.

At 4° C. BrCN was more efficient, yielding 95% circular product while EDC yielded only 55% product. However, at 25° C. both EDC and BrCN yielded 95% product. Therefore, BrCN is more effective at lower temperatures but either EDC or BrCN can be used with equal success at 25° C. However, BrCN has an additional advantage over EDC since ligation with BrCN requires 24 hr or less while ligation with EDC requires about 4 days.

Use of a 5'- or 3'-Phosphate

Under different ligation conditions joining a 3'-phosphate with a 5'-OH yielded more ligated product than joining a 5'-phosphate with a 3'-OH (Ashley, et al.).

Therefore, the percent conversion to circular oligonucleotide 6 (FIG. 3) by a 5'-phosphate or by a 3'-phosphate precircles was compared:

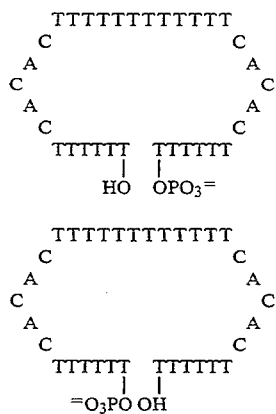

Circularization reactions were performed using a dA$_{12}$ end-joining-oligonucleotide and the established optimal conditions, except that 5 nmoles of precircle and end-joining-oligonucleotide were used. Products were visualized under UV light after separation by denaturing gel electrophoresis.

Conversion to circular product was 60% (±5%) when a 5'-phosphate was present and 95% when a 3'-phosphate was present. No increase in yield was observed when increased reaction times or increased reagent concentrations were used.

Accordingly, use of a 3'-phosphate rather than a 5'-phosphate improves circularization.

EXAMPLE 2

Circular Oligonucleotides Bind Target Nucleic Acids with Higher Affinity Than Do Linear Oligonucleotides The binding affinities of circles 6 and 7 (SEQ ID NO: 5 and SEQ ID NO:6, respectively) for their targets were measured by comparison of the melting temperatures of the circular and linear complexes. Solutions contained 1:1 ratios of oligonucleotide and target (3 μM each) in 100 mM NaCl, 10 mM MgCl$_2$, and 10 mM Tris-HCl (pH 7.0). Mixing curves measured at 260 nm confirmed that 1:1 complexes were formed. The free energies ($-\Delta G°_{37}$) of the complexes were derived from the melting data using a two-state curve-fitting method (Petersheim, et al., 1983, Biochemistry 22: 256).

The results showed that the circular oligonucleotides bound to their targets more strongly than did linear precircles or Watson-Crick complementary target-sized oligonucleotides (Table 2). For example, target 4 (SEQ ID NO: 8) formed a duplex with its target-sized Watson-Crick complement having a $T_m$ of 37.1° C. while the precircle 1:target 4 complex (i.e. SEQ ID NO: 5 bound to SEQ ID NO: 8) had a $T_m$ of 44.7° C. By comparison, circle 6, having the same sequence as precircle 1, bound to target 4 with a $T_m$ of 57.5° C. and a free energy of binding that was 8.6 kcal/mol more favorable than the corresponding Watson-Crick duplex. The corresponding association constant at 37° C. is $6 \times 10^{11}$ $M^{-1}$, which is more than six orders of magnitude greater than for the Watson-Crick duplex. A similar effect was observed for the binding of circle 7 (SEQ ID NO: 6) to target 5 (SEQ ID NO: 9); this complex had a $T_m$ of 62.3° C., whereas the corresponding Watson-Crick duplex melted at 43.8° C. These data indicate that the binding of circular oligonucleotides is stronger than the binding of a linear oligonucleotide to a target.

To determine the binding characteristics when the target sequence was embedded within a longer sequence, a 36 nucleotide oligonucleotide was synthesized with a 12 base target sequence (equivalent to target 4) in the middle. Melting studies revealed that circle 6 bound to this longer oligonucleotide more strongly than it did to a target having the same size as the binding domains of the circle: the Tm of circle 6 with target 4 was 59.8° C. whereas with the 36 base oligonucleotide containing an embedded target the Tm was 63.4° C. Therefore the binding strength of circles with embedded targets was higher than that with binding-domain-sized-targets.

The binding affinity of circle 6 for an RNA target was tested by synthesizing oligoribonucleotide $rA_{12}$ and determining the $T_m$ of circle 6 with $rA_{12}$. The $T_m$ of circle 6 with $rA_{12}$ was 58.3° C. compared with 57.8° C. with $dA_{12}$. The data indicate that circles bind to RNA targets as strongly or more strongly than as to DNA targets.

TABLE 2

| oligonucleotide:target | complex | $T_m$, °C. | $-G°_{37}$ (kcal/mol) |
|---|---|---|---|
| | 3'-TTTTTTTTTTTT<br>5'-AAAAAAAAAAAA | 37.1 | 8.1 |
| | 3'-TTCTTTTCTTTC<br>5'-AAGAAAAGAAAG | 43.8 | 10.3 |
| 1:4 | <pre>   TTTTTTTTTTTT
  C            C
 A              A
C  AAAAAAAAAAAA  C
 A              A
  C            C
   TTTTTT TTTTTT
         |
        OPO3=</pre> | 44.7 | 10.5 |
| 3:5 | <pre>   TTCTTTTCTTTC
  C            C
 A              A
C  AAGAAAAGAAAG  C
 A              A
  C            C
   TTCTTT TCTTTC
         |
        OPO3=</pre> | 47.0 | 10.8 |
| 6:4 | <pre>   TTTTTTTTTTTT
  C            C
 A              A
C  AAAAAAAAAAAA  C
 A              A
  C            C
   TTTTTTTTTTTT</pre> | 57.4 | 16.7 |
| 7:5 | <pre>   TTCTTTTCTTTC
  C            C
 A              A
C  AAGAAAAGAAAG  C
 A              A
  C            C
   TTCTTTTCTTTC</pre> | 62.3 | 16.4 |

EXAMPLE 3

Circular Oligonucleotides Bind Target More Selectively Than Linear Oligonucleotides In order to measure the sequence selectivity of circular oligonucleotides, a set of target oligonucleotides with one variable base was constructed. Binding energies for a circle complexed with these targets were measured; the selectivity was defined by the free energy difference between the correct sequence and mismatched sequences. The selectivity obtained with the circular structure was then directly compared to the selectivity of an analogous linear oligonucleotide.

DNA oligonucleotides were machine synthesized using the β-cyanoethyl phosphoramidite method. Circular oligonucleotide 8 was prepared from a linear precircle having SEQ ID NO: 7:

5'-pTCTTTCCACACCTTTCTTTTCTT-CACACTTCTTT and was cyclized by assembly around an end-joining oligonucleotide having the sequence 5'-AAGAAAAGAAAG (SEQ ID NO: 9) using BrCN/imidazole to close the final bond, as described in Example 1. The circular structure was confirmed by its resistance to a 3'-exonuclease and 5'-phosphatase.

The sequence selectivity of circle 8 was measured by hybridizing it with targets which contained a single mismatched base and determining the strength ($\Delta G°_{37}$) of the resulting complexes by thermal denaturation.

Eight targets were synthesized which were complementary to circle 8 and linear oligonucleotide 9 except for a single centrally positioned variable base (X or Y =A, G, C, T). Four targets have a variable base X which is matched with two opposing T's in the circle, resulting in a T-X-T triad. In the remaining four targets, the variable base Y is matched with two opposing C's in the circle, giving a C-Y-C triad. For comparison to this circle complex, a linear oligonucleotide 9 was used; resulting in a duplex with a central T-X pair in the first four experiments or a C-Y pair in the remaining four.

| complex (X, Y = A, T, G, C) | expt. no. |
|---|---|
| 3'-T T C T T T T C T T T C<br>5'-A A G A X A A G A A A G | 1-4 |
| A C T T C T T T T C T T T C C A<br>C  A A G A X A A G A A A G  C<br>A C T T C T T T T C T T T C C A | 5-8 |
| 3'-T T C T T T T C T T T C<br>5'-A A G A A A A Y A A A G | 9-12 |
| A C T T C T T T T C T T T C C A<br>C  A A G A A A A Y A A A G  C<br>A C T T C T T T T C T T T C C A | 13-16 |

Thermal denaturation of the sixteen complexes was carried out in the presence of 10 mM MgCl$_2$, 100 mM NaCl, and 10 mM Tris. HCl (pH 7.0), with target and circular or linear oligonucleotide concentrations at 3 µM each. Experiments were carried out in duplicate and the results averaged. Oligonucleotide:target complex melting was monitored at 260 nm. The temperature vs. absorbance curves so generated show a single transition from bound to free oligonucleotide. Free energies of association were obtained by fitting the data with a two-state curve-fitting method. The results were checked in two cases by measuring the association energies by the van't Hoff method, good agreement was seen between the two methods. Selectivities are defined as the difference in free energies (ΔG) of complexation between matched and mismatched oligomers.

Table 3 displays the results of the mismatch experiments. Experiments 1-4 show the effects of a T-X target mismatch on a DNA duplex. As expected, the true match (X=A) gives the most favorable complex ($-\Delta G°_{37}$=10.3 kcal/mol); the mismatches (X=G, C, T) result in a loss of 3.2-4.4 kcal/mol in binding energy, in good agreement with published mismatch studies. Experiments 5-8, by comparison, show the effects of a T-X-T mismatch on circle complex binding strength. Once again, the true match (X=A) gives the most favorable three stranded complexes ($-\Delta G°_{37}$=16.4 kcal) However, target mismatches (X=G, T, C) result in a considerably larger loss of binding energy (6.2-7.6 kcal/mol) for a circular oligonucleotide than for a linear oligonucleotide.

Similarly, experiments 9-12 give the effects of a C-Y mismatch on the two stranded duplex. The matched base (Y=G) gives a free energy of duplex association of −10.3 kcal/mol. The mismatches (Y=A, T, C) result in a loss of 5.2 to 5.8 kcal/mol of binding energy, in reasonable agreement with published data. By contrast, the effects of a C-Y-C mismatch are greater in a three stranded complex (experiments 13-16): the match (Y=G) gives a binding energy of −16.4 kcal/mol, and the mismatches (Y=A, T, C) are less stable by 7.1 to 7.5 kcal/mol.

Thus, in all the cases studied, the circular ligand shows greater selectivity for its correctly matched sequence than does the standard linear oligomer. The selectivity advantage ranges from 1.3 to 2.2 kcal/mol for the C-Y-C series to 3.0 to 3.4 kcal/mol for the T-X-T series. These are quite significant differences, considering they arise from a single base change; in the T-X-T series, the circular oligonucleotide is nearly twice as selective as the linear oligonucleotide. This selectivity difference corresponds to one to two orders of magnitude in binding constant at 37° C.

There are two factors which may explain this high selectivity. First, because two domains of the circular oligonucleotide bind the central target strand, the circular oligonucleotide, in effect, checks the sequence twice for correct matching. Secondly, protonation of cytosine within a C+G−C triad may also be a factor in increasing selectivity. This protonation is likely to be favored only when there is base triad formation wherein guanine can share the positive charge; evidence suggests that the pKa of cytosine within a base triad is 2-3 units higher than that of free deoxycytosine. The addition of this positive charge may lessen the negative charge repulsions arising from the high density of phosphates in the complex and thereby increase binding stability.

Therefore, circular oligonucleotides, as described herein, to have both higher binding affinity and higher selectivity than can be achieved with Watson-Crick duplexes alone.

TABLE 3

|  | expt. # | variable base | $T_m$, °C. | $-\Delta G°_{37}$ (kcal/mol) | Selectivity (kcal/mol) |
|---|---|---|---|---|---|
| duplex | 1 | X=A | 43.8 | 10.3 | — |
|  | 2 | X=G | 33.8 | 7.1 | 3.2 |
|  | 3 | X=C | 28.3 | 5.9 | 4.4 |
|  | 4 | X=T | 31.1 | 6.4 | 3.9 |
| circle complex | 5 | X=A | 62.3 | 16.4 | — |
|  | 6 | X=G | 44.2 | 10.2 | 6.2 |
|  | 7 | X=C | 39.8 | 8.8 | 7.6 |
|  | 8 | X=T | 40.8 | 9.1 | 7.3 |
| duplex | 9 | Y=A | 26.2 | 5.1 | 5.2 |
|  | 10 | Y=G | 43.8 | 10.3 | — |
|  | 11 | Y=C | 22.2 | 4.5 | 5.8 |
|  | 12 | Y=T | 27.0 | 5.0 | 5.3 |
| circle complex | 13 | Y=A | 39.9 | 9.0 | 7.4 |
|  | 14 | Y=G | 62.3 | 16.4 | — |
|  | 15 | Y=C | 41.3 | 9.3 | 7.1 |
|  | 16 | Y=T | 39.6 | 8.9 | 7.5 |

EXAMPLE 4

Factors Effecting Complex Formation

Figure 5:
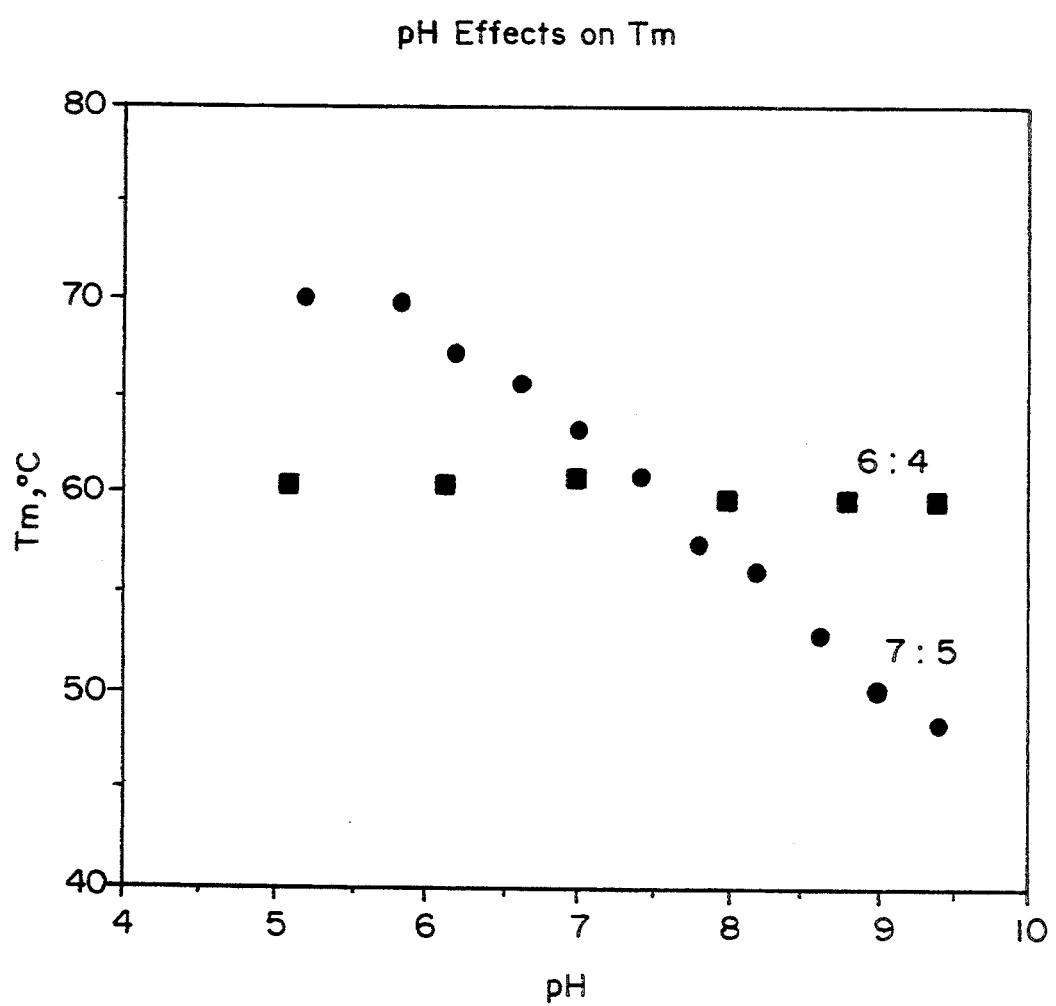

1) Solution effects. The effects of NaCl, Mg$^{2+}$, spermine, and pH on circle:target complexes were examined. Circles with cytosines in the binding domains are sensitive to pH, and exhibited greater stability at lower pH values. However, these and other circle:target complexes are quite stable at the physiological pH of 7.0-7.4 (FIG. 5). The complexes show salt concentration sensitivity comparable to duplexes; however, small amounts of Mg$^{2+}$ or spermine increase the complex stability markedly. For example, in a concentration of 1 mM Mg$^{++}$ at pH 7.0, with no added salts, a stable 7:5 circle:target complex formed having a Tm of 58° C. When a solution of 20 µm spermine containing no added salts was used the 7:5 complex again formed stably with a Tm of 56° C. Both Mg$^{++}$ and spermine are present in at least these concentrations in mammals, and so circle:target complexes will be stable under physiological conditions.

2) Loop size. The optimum number of nucleotides for the loop domain of a circle was determined by observing complex formation between a target and circles with different loop sizes. Precircle linear oligonucleotides similar to precircle 1 were synthesized with 2, 3, 4, 5, 6 and 10 base loops using an arbitrary sequence of alternating C and A residues. Each of these precircles was designed to bind to the $A_{12}$ template (i.e. target 4 (SEQ ID NO: 8)). The $T_m$'s for circles with 4, 5, 6 and 10 base loops showed that a five-nucleotide loop size was optimum for the circle binding either to template A12 or to a longer 36mer sequence containing the $A_{12}$ binding site (see FIG. 6A).

Figure 6B:
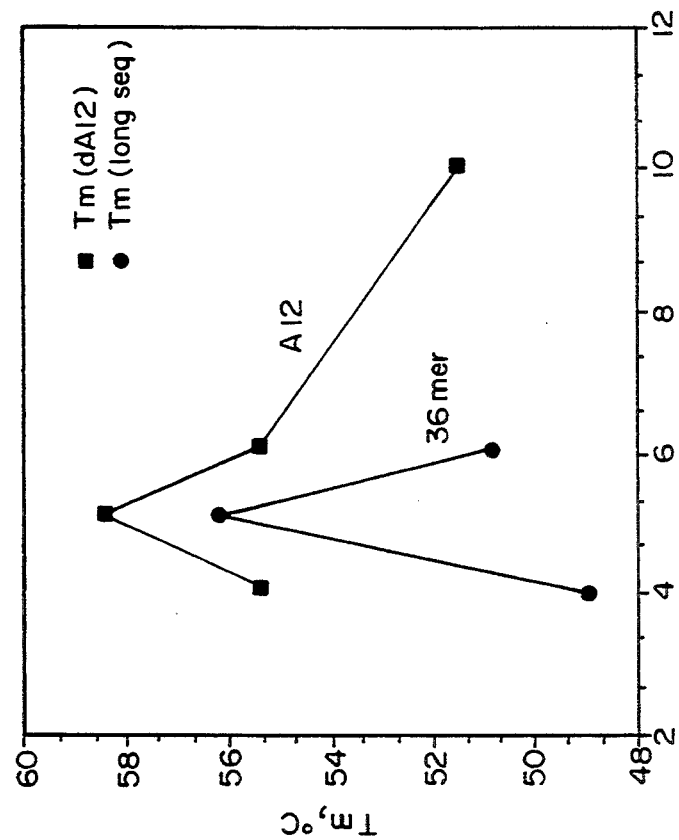
FIG. 6B depicts the effect of target and binding domain length on complex formation.
Figure 6A:
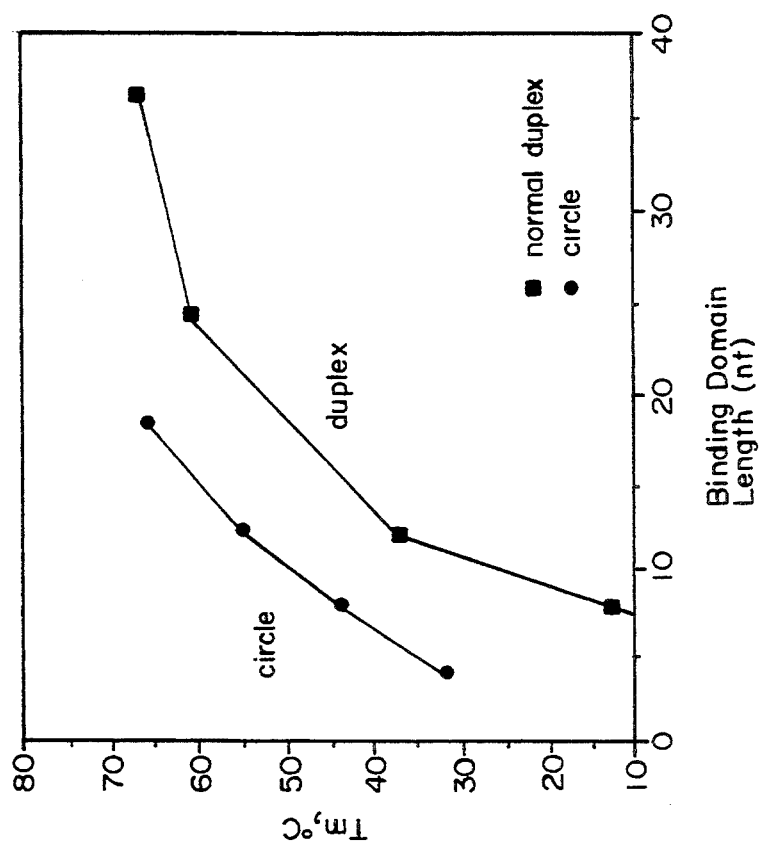
FIG. 6A depicts the effect of loop size on complex formation, with a comparison between binding to two targets: a simple $(dA)_{12}$ target (squares) and a 36 nucleotide oligonucleotide target (circles).
Figure 7:
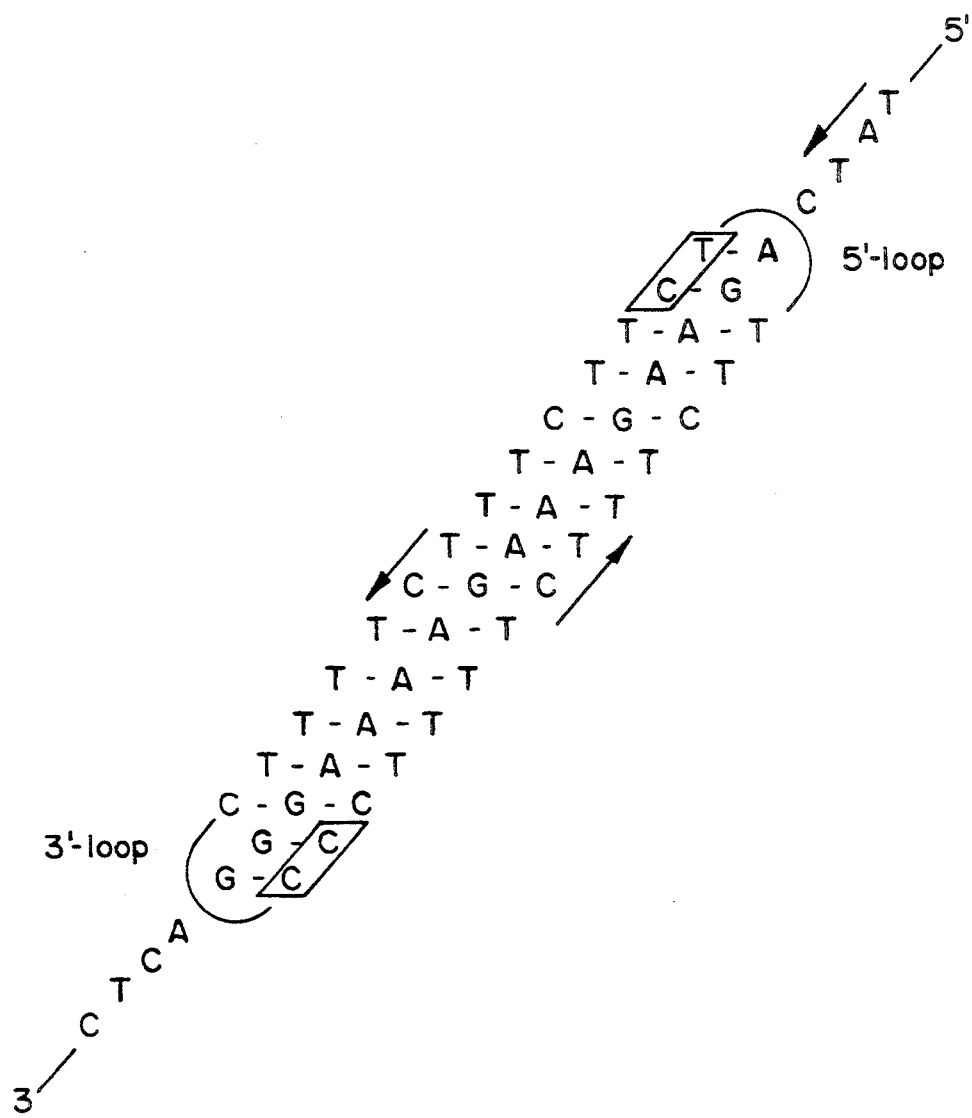
FIG. 7 depicts a complex formed between a circular oligonucleotide and a target where the P and AP binding domains are staggered on the target.

3) Binding Domain length. The effect of circular oligonucleotide binding domain length on circle:target complex melting temperature was compared to melting of duplexes having the same length. Circles with various size binding domains were constructed and complexed with single-stranded $dA_n$ targets for n equal to 4, 8, 12 and 18 nucleotides. FIG. 6B illustrates that considerably higher $T_m$'s were observed for circle:target complexes relative to Watson-Crick duplexes having the same length as the binding domains (determined in 0.1M NaCl, pH 7). For example, a 12-base circular complex melted at about the same temperature as a 24-base duplex. The 4-base circular complex melted at 34° C., whereas the corresponding Watson-Crick duplex $T_m$ was less than 0° C.

4) Methylation. It has been known for some time that methylation at the C-5 position of cytosine, forming the naturally-occurring base $m^5C$, raises the $T_m$ of duplex DNA in which it occurs, relative to unmethylated sequences (Zmudzka et al., 1969, Biochemistry 8: 3049). In order to investigate whether addition of this methyl group would stabilize circle:target complexes, two analogs of circle 7 (having SEQ ID NO: 6) were synthesized. In one circle, the six C's in the binding domains were methylated leaving the loop unmethylated ($Me_6$). In the second circle, all twleve C's were methylated ($Me_{12}$). Melting temperatures for the complexes of these methylated circle with target 5 were measured. The $Me_6$ complex had a $T_m$ of 71.1° C. (compared to 61.8° C. for the unmethylated circle), and the $Me_{12}$ circle had a $T_m$ of 72.4° C. Thus, use of the natural base $m^5C$ in place of C increased stability substantially, and in one case resulted in a 12-base complex which melted 10.6° C. higher than an unmethylated circle and 28.6° C. higher than the corresponding unmethylated Watson-Crick duplex.

EXAMPLE 5

Replacement of Nucleotide Loop Domains with Non-Nucleotide Loop Domains

The loop domains of circular oligonucleotides were replaced with polyethylene or oligoethylene glycol chains of different lengths and the effect of such synthetic loops upon circular oligonucleotide binding and nuclease resistance was assessed.

Methods

Circular oligonucleotides were synthesized having tetra-, penta-, or hexa-ethylene glycol chain loop domains. In each case the ethylene glycol chain was synthetically prepared for automated DNA synthetic procedures using the method of Durand et al. (1990, Nucleic Acids Res. 18: 6353-6359). Briefly, a phosphoramidite was placed on a hydroxy group at one end of the ethylene glycol chain and a dimethoxytrityl (DMT) moiety was placed on the other terminal ethylene glycol hydroxy group. This derivatized ethylene glycol chain was then added to the growing linear oligonucleotide at the appropriate step of automated DNA synthesis. Circularization steps were performed by procedures described in Example 1. A linear oligonucleotide precircle having a tetraethylene loop domain was not efficiently circularized. This result indicates that a tetraethylene loop domain may be too short for optimal binding to a target.

Two types of linear oligonucleotides were used as target binding domains for the circular oligonucleotides: Target I was a 12-base oligonucleotide having no non-target nucleotides and Target II was a 36-base oligonucleotide having a 12-base target within it. The target sequences utilized were 5'-AAGAAAAGAAAG-3' (SEQ ID NO: 9) and 5'-AAAAAAAAAAAA-3'(SEQ ID NO: 8), the latter is termed a poly(dA)$_{12}$ target sequence.

The melting temperatures (Tm) of circular oligonucleotides with polyethylene loops were observed at pH 7.0 (10 mM Tris-HCl) in 10 mM $MgCl_2$ and 100 mM NaCl. Each linear target and each circular oligonucleotide was present at a 3 μM concentration.

Results

The $T_m$ of a circular oligonucleotide having a CACAC nucleotide loop sequence and a poly(dT)$_{12}$ sequence for both P and AP domains was 57.8° C. when bound to a poly (dA)$_{12}$ target sequence. The Tm of a circular oligonucleotide having the same P and AP domain sequences but hexaethylene glycol loop domains was 51.4° C. when bound to the same target.

A comparison of Tm values observed for circular oligonucleotides having pentaethylene glycol (PEG) and hexaethylene glycol (HEG) loop domains is depicted in Table 4.

TABLE 4

| Complex | Target I Tm | Target II Tm |
|---|---|---|
| pTTCTTTTCTTTCp<br>PEG  AAGAAAAGAAAG PEG<br>pTTCTTTTCTTTCp | 51.5 | 47.5 |
| pTTCTTTTCTTTCp<br>HEG  AAGAAAAGAAAG HEG<br>pTTCTTTTCTTTCp | 58.0 | 51.1 |
| pTTTTTTTTTTTTp<br>HEG  AAAAAAAAAAAA HEG<br>pTTTTTTTTTTTTp | 51.4 | 46.5 |

The Tm value observed for a circular oligonucleotide having a HEG loop is about 4.5° C. higher than that of a circular oligonucleotide with a PEG loop. Therefore, circular oligonucleotides with hexaethylene glycol loop domains bind with greater stability than do circular oligonucleotides with tetra- or penta-ethylene glycol loops.

Nuclease Resistance

Circular oligonucleotides were tested for nuclease resistance when unbound and when bound to a target oligonucleotide. All circular oligonucleotides, whether bound or unbound, were completely resistant to exonucleases. Endonuclease sensitivity was assessed using S1 nuclease according to the manufacturer's suggestions.

A comparison of the resistance of bound and unbound circular oligonucleotides to S1 nuclease is depicted in Table 5.

TABLE 5

| Oligonucleotide Cleavage | Time For 50% S1 |
|---|---|
| ┌─p T T C T T T T C T T T C p─┐<br>HEG ⎰ ⎱ HEG<br>└─p T T C T T T T C T T T C p─┘ | 1 min. |
| ┌─p T T C T T T T C T T T C p─┐<br>HEG   A A G A A A A G A A A G   HEG<br>└─p T T C T T T T C T T T C p─┘ | >24 h |
| A C T T C T T T T C T T T C C A<br>C                                       C<br>A C T T C T T T T C T T T C C A | |
| A C T T C T T T T C T T T C C A<br>C   A A G A A A A G A A A G   C<br>A C T T C T T T T C T T T C C A | 40 min. |

These data indicate that unbound circular oligonucleo-tides are vulnerable to S1 nuclease. However, when bound to a target, a circular oligonucleotide having a polyethylene loop domain is much more resistant to S1 nuclease, at least 36-fold more resistant, than a circular oligonucleotide with a nucleotide loop domain.

The nuclease resistance of circular and linear oligonucleotides was also compared when these oligonucleotides were incubated in human plasma for varying time periods. Circular oligonucleotide 7 and the precursor to this circle, linear oligonucleotide 2, were incubated at a 50 μM concentration in plasma at 37° C. Aliquots were removed at various time points and cleavage products were separated by gel electrophoresis. Nuclease resistance was assessed by observing whether degradation products were evident on the gels.

When incubated in human plasma the half-life of linear oligonucleotide 2 was 20 min. In contrast, circular oligonucleotide 7 underwent no measurable nuclease degradation during a 48 hr incubation. Accordingly, the half-life of a circular oligonucleotide is greater than 48 hr in human plasma, i.e. more than 140 times longer than a linear oligonucleotide having an equivalent sequence.

EXAMPLE 6

CIRCULAR OLIGONUCLEOTIDES CAN SELECTIVELY BIND TO RNA

Experiments described in this example indicate that, unlike linear oligonucleotides, circular oligonucleotides can preferentially bind to an RNA, rather than a DNA, target.

Two linear deoxyoligonucleotides were prepared as targets, a "T" (SEQ ID NO.: 11) target and a "dU" (SEQ. ID. No.: 12) target:

T target: 5'-A A G A A T A G A A A G-3'; and dU target: 5'-A A G A A U A G A A A G-3'.

A circular oligonucleotide having SEQ ID NO.: 14 was also prepared:

```
      T T C T T C T C T T T C
    C                          C
   A                            A
  C                              C
   A                            A
    C                          C
      T T C T T A T C T T T C    .
```

For comparison, a linear oligonucleotide complementary to the T and dU targets was also synthesized (i.e. the linear oligonucleotide, SEQ ID NO.: 13):

5'CTTTCTATTCTT3'.

The melting temperatures (Tm) values observed for the circular vs linear oligonucleotide binding to each of the targets is presented in Table 6.

TABLE 6

| | Tm Values for Oligonucleotides | |
|---|---|---|
| Targets | Linear | Circular |
| T target | 42.9° C. | 41.1° C. |
| dU target | 40.9° C. | 42.9° C. |

The linear oligonucleotide binds more strongly to the T target than to the dU target, by an amount which is significantly larger than experimental error limits. This difference in Tm values corresponds to a difference in free energy of binding of 1.7 kcal/mole.

However, in contrast to the linear oligonucleotide, the circular oligonucleotide binds more strongly to the U target. Therefore, the circular oligonucleotide can exhibit a preference for an RNA target relative to the corresponding DNA target.

Moreover, the increase in binding strength for a circular oligonucleotide to the RNA target corresponds to a free energy difference of 0.8 kcal/mole which indicates that at 37° C. an RNA target would be preferred by about 3:1 over a corresponding DNA target.

EXAMPLE 7

Strand Replacement By Circular Oligonucleotides

Circular oligonucleotide 6 (FIG. 3) bound to a dA$_{12}$ target with 9 kcal/mole greater stability than did a linear dT$_{12}$ oligonucleotide (Example 2). This increase in stability demonstrates that a circular-oligonucleotide:target complex is thermodynamically favored over a linear-oligonucleotide:target. In addition, a circular oligonucleotide can actually accelerate (or catalyze) dissociation of duplex DNA target sequences to form a complex with one strand of the duplex.

To test whether a circular oligonucleotide can readily dissociate duplex DNA and displace one strand of a duplex DNA target, the kinetics of strand displacement were observed for a duplex DNA target in the presence of a complementary linear or circular oligonucleotide.

A DNA duplex target with a fluorescein group on one strand and a tetramethylrhodamine group on the other strand was prepared using published procedures (Cardullo et al. 1988 Proc. Natl. Acad. Sci. USA 85: 8790; Cooper et al. 1990 Biochemistry 29: 9261). The structure of the duplex target (SEQ ID NO.: 15) was as follows:

5'-fluorescein-A A A A A A A A A A A
3'-rhodamine-T T T T T T T T T T T.

The Tm of this labeled duplex target was normal, therefore the fluorescent substituents had no significant effect upon association kinetics. Moreover, the emission maxima of the fluoescein-dA$_{12}$ strand was 523 nm while the emission maxima of the rhodamine-dT$_{12}$ strand was 590 nm, allowing the association kinetics of the two strands could be separately monitored.

Strand displacement reactions were done at 10° C. in a 1 cm fluorescence cuvette. Reaction conditions were 100 mM NaCl, 10 mM Mg Cl$_2$ and 10 mM Tris-HCl, pH 7.0 with a reaction volume of 3 ml. Labeled duplex was allowed to equilibrate for at least 1 hr at 10° C. before addition of a 40-fold excess of linear or circular oligonucleotide (final concentration 0.01 μM). A Spex Flurolog F 111A fluorescence instrument with 5 mm slit widths was used. An excitation wavelength of 450 nm and a monitored emission wavelength of 523 nm was used. The results were independent of both excitation and monitored emission wavelengths. Reactions were followed for at least 5 half-lives.

Addition of rhodamine-dT$_{12}$ to fluorescein-dA$_{12}$ caused a decrease in fluorescein fluorescence and an increase in rhodamine fluorescence. Such effects are due to energy transfer between the fluorescent moieties (Cardullo et al.).

The association rate constant of the two fluorescently-labeled strands was determined by mixing the strands under pseudo-first order conditions and monitoring the rate of decrease in fluorescein emission. At 10° C. the observed association constant was $3.2 \times 10^6 \, M^{-1} \, sec^{-1}$, which agrees well with published rates of association for DNA oligonucleotides (Nelson et al. 1982 Biochemistry 21: 5289; Turner et al. 1990 in *Nucleic Acids* (subvolume C), W. Saenger, Ed. Springer-Verlag, Berlin: 201-227).

To compare the rates at which a single linear strand (SEQ ID NO.: 8) or a circular oligonucleotide having SEQ ID NO.: 5 (i.e. circular oligonucleotide 6) exchanged with strands in a duplex DNA, an excess of an unlabeled linear or circular oligonucleotide was mixed with the fluorescently-labeled duplex DNA target. The increase in fluorescein emmission was then observed at a temperature significantly below the Tm of the duplex target as a measure of duplex target strand dissociation.

Figure 8:
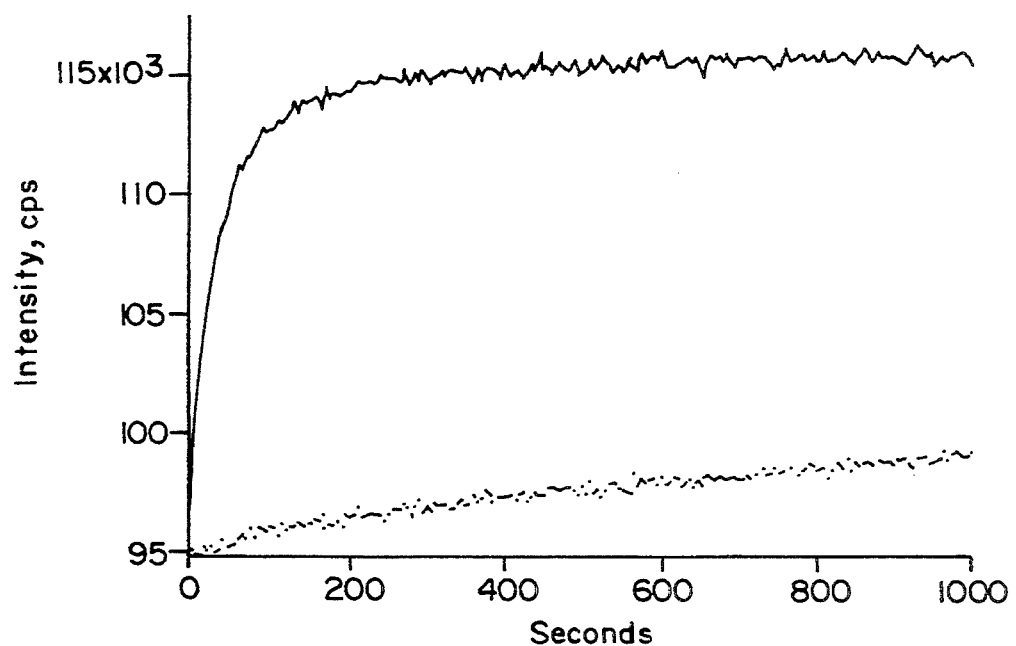
FIG. 8 depicts replacement of one strand of a fluorescently labeled double stranded target (SEQ ID NO: 11) by either a linear oligonucleotide having SEQ ID NO: 8 (dotted line) or a circular oligonucleotide having SEQ ID NO: 5 (solid line). Strand replacement was measured by an increase in fluorescein fluorescence intensity (Y-axis) as a function of time (X-axis).

FIG. 8 depicts a typical kinetic assay for the dissociation of duplex target by a 40-fold excess of unlabeled dA$_{12}$ (dotted line) or circular oligonucleotide 6 (solid line) at 10 ° C. As depicted, duplex target dissociation by the circular oligonucleotide is considerably faster than is the dissociation by the linear oligonucleotide. The first order rate constant for dissociation by the linear oligonucleotide is $2.0 \times 10^{-4} \, sec^{-1}$ whereas the first order rate constant for dissociation by the circular oligonucleotide is $2.3 \times 10^{-2} \, sec^{-1}$, almost two orders of magnitude faster. This difference is even more apparent when the half-lives for the target duplex in the presence of linear vs circular oligonucleotides are calculated. At 10° C., the duplex has a half-life for dissociation of 58 min in the presence of the linear oligonucleotide but only 30 sec in the presence of the circular oligonucleotide.

Unlike the rate of reaction between linear oligonucleotide and duplex, the rate of reaction between the circular oligonucleotide and duplex is dependent on the concentration of added circular oligonucleotide at low concentrations, and shows Michaelis-Menten type saturation behavior at higher concentrations (FIG. 9).

The dissociation rate of labeled duplex at 10° C. can be derived from the duplex association rate constant and $\Delta G°_{10}$ values This rate constant, $8.5 \times 10^{-10} \, sec^{-1}$, is consistent with rates derived from predicted thermodynamic parameters for a duplex complex (Breslauer et al. 1986 Proc. Natl. Acad. Sci. USA 83: 3746) although this rate is significantly slower than the rate constant for strand displacement by a linear oligonucleotide. An increase in duplex dissociation upon addition of a linear oligonucleotide has been noted in other cases (Chamberlin et al. 1965 J. Mol. Biol. 12: 410). Comparison of the rate for the circular oligonucleotide-catalyzed reaction over that of the unassisted duplex dissociation reveals a rate enhancement of about $10^7$ fold (Sigler et al. 1962 J. Mol. Biol. 5: 709).

A double reciprocal plot of 1/[circular oligonucleotide] vs. $1/k_{obs}$ is linear and yields a $k_{cat}$ of $0.024 \pm 0.005$ sec$^{-1}$ and a $K_M$ of $2.2 \times 10^{-7}$M. The $k_{cat}$ is 100-fold greater than the observed rate constant obtained for the reaction of the duplex with either dA$_{12}$ or dT$_{12}$ single strands.

The observed saturation behavior (FIG. 9) suggests that a complex forms between the circle and the double-stranded target. Using the above $K_M$ value and assuming that $k_{cat} << k_{-1}$, where $k_{-1}$ is the dissociation rate constant for this complex, the free energy of association is $-8.6 \, kcal.mol^{-1}$ at 10° C. This value is similar to an estimated value of about $-9 \, kcal.mol^{-1}$ for the P domain in a 12-base triple helix consisting of T.A-T base triads, as derived from the thermodynamic parameters of Pilch et al. (1990 Nucleic Acids Res. 18: 5743).

EXAMPLE 8

Binding Properties of a Circular Oligonucleotide Having More Than One Pair of Binding Domains A circular oligonucleotide having two pairs of binding domains was synthesized. Such a circular oligonucleotide selectively bound one of two targets depending upon the pH of the hybridization reaction.

Materials and Methods

Oligonucleotide Synthesis

Oligonucleotides were synthesized using β-cyanoethylphosphoramidite chemistry (Beaucage et al. 1981Tetrahedron Lett. 22: 1859). The concentration of oligonucleotide was determined by absorbance at 260 nm; extinction coefficients were calculated by the nearest neighbor method (Borer 1975 in *Handbook of Biochemistry and Molecular Biology* G. D. Fasman, ed. CRC Press: Cleveland, p. 589).

An oligonucleotide having SEQ ID NO:16 (5'-dTCTCTTTTTTTTTTTCTCTCTCTTTTTTTTT-TTCTCp) was synthesized and circularized by the template-directed cyclization reaction described in Example 1 and in Prakash et al. (1992 J. Am. Chem. Soc. 114: 3523). The end-joining-oligonucleotide employed for circularization had SEQ ID NO:17 (5'-dAAAGAGAGAGAAA). Conversion to circle was greater than or equal to 95% as assessed by UV-shadowing of the reaction mixture electrophoresed through a 20% denaturing polyacrylamide gel.

The circular oligonucleotide product having SEQ ID NO:18 was obtained from a polyacrylamide gel slice containing the slower moving band. To purify the circular oligonucleotide, the gel slice was crushed and dialyzed against water. The circularity of the oligonucleotide was tested by exposing the preparation to an exonuclease (T4 polymerase, Promega) under conditions leading to complete degradation of a linear oligonucleotide to mononucleotides. The SEQ ID NO:18 oligonucleotide was completely resistant to such exonuclease treatment.

The SEQ ID NO:18 circular oligonucleotide contained two pairs of nine base binding domains. One pair of binding domains (pair I) bound a target oligonucleotide having SEQ ID NO:19 (5'-dAGAGAGAGA), while the other pair of binding domains (pair II) bound a target oligonucleotide having SEQ ID N0:20 (5'-dAAAAAAAAA).

A thirty three nucleotide oligonucleotide was also synthesized which contained two target binding sites, one for the pair I and one for the pair II binding domains of the SEQ ID NO:18 circular oligonucleotide. This thirty three nucleotide oligonucleotide had SEQ ID NO:21 i.e. 5'-dCACAAGAGAGAGAATCCCTAAAAAAAAAAACAC wherein the two target sites are indicated by underlining.

Two linear oligonucleotides complementary to the target sites within the SEQ ID NO:21 oligonucleotide were also synthesized: an oligonucleotide having SEQ ID NO:22 (5'-dTCTCTCTCT) and an oligonucleotide having SEQ ID NO:23 (5'-dTTTTTTTTT).

Thermal Denaturation Procedures

Thermal denaturation experiments with the circular oligonucleotide having SEQ ID NO:18 and the two target oligonucleotides having SEQ ID NO:19 and SEQ ID NO:20 were performed as described in Example 2. In particular, 1.5 µM of target oligonucleotide and 1.5 µM of circular oligonucleotide was placed in a buffer containing 100 mM NaCl, 10 mM MgCl$_2$ and 10 mM Na-PIPES (from Sigma Chemical Co.). To assess the effect of pH upon binding, thermal denaturation experiments were performed using pH values varying from 5.5 to 9.0.

To generate thermal denaturation profiles of hyperchromicity vs. temperature the reaction mixture was first placed in a 1 cm-pathlength stoppered quartz microcell under nitrogen. The absorbance of the reaction mixture was recorded at 260 nm using a Cary 1 spectrophotometer when the temperature was increased at a rate of 0.5° C./min. The $T_m$ was assigned as the temperature of the inflection point in the denaturation curve. Measurement precision was ±0.5° C. as determined by observation of $T_m$ variability in several experiments.

Stoichiometric Determinations

The proportion of SEQ ID NO:18 circular oligonucleotide added to either SEQ ID NO:19 or SEQ ID NO:20 targets was varied in mixing experiments to determine the mole fraction of circular oligonucleotide present at complete complexation of target with circular oligonucleotide. To detect binding by observing a change in hyperchromicity using absorbance readings at 260 nm, the total DNA concentration was maintained at 4.5 µM while the proportion of circular oligonucleotide to target was varied.

Under such conditions, a change in the slope of the observed absorbance vs circular oligonucleotide mole fraction indicates that no further binding of target will occur as the proportion of circular oligonucleotide is increased. Therefore the inflection point in such a curve provides the mole fraction at which complete complexation has occurred. If the inflection point is approximately 0.5 then half of the oligonucleotide present in the hybridized complex is the circular oligonucleotide and half is a target oligonucleotide. Accordingly a mole fraction of about 0.5 for complete complexation indicates the stoichiometry of circular oligonucleotide to target is 1:1.

When the mole fraction for complete complexation is greater than 0.5, more circular oligonucleotide than target oligonucleotide is present in the complex, e.g., a mole fraction of 0.67 means that two circular oligonucleotides are present per target. Therefore the stoichiometry of circular oligonucleotide to target in the complex will be greater than 1:1. Similarly, when the mole fraction for complete complexation is less than 0.5, less circular oligonucleotide than target oligonucleotide is present in the complex and the stoichiometry of circular oligonucleotide to target will be less than 1:1, e.g. a mole fraction of 0.3.3 means that one circular oligonucleotide and two targets are present.

Binding of SEQ ID NO:18 Circular Oligonucleotide to SEQ ID NOS:19-21 Targets

At pH 7.0 the circular oligonucleotide having SEQ ID NO:18 bound target SEQ ID NO:19 with a $T_m$ of 44.5° C. (FIG. 10A, open circles) and an estimated free energy of association at 37° C. of −11.2 kcal/mole. Under similar conditions the circular oligonucleotide (SEQ ID NO:18) bound target SEQ ID NO:20 with a $T_m$ of 47.5° C. (FIG. 10A, filled circles) and a free energy of association at 37° C. of −13.2 kcal/mole. Accordingly the circular oligonucleotide had roughly the same affinity for target SEQ ID NO:19 and SEQ ID NO:20.

FIG. 10B depicts the mole fraction of SEQ ID NO:18 circular oligonucleotide present in a mixture of target and circular oligonucleotide versus the absorbance of that mixture. The mole fraction of SEQ ID NO:18 circular oligonucleotide when fully complexed with SEQ ID NO:19 target (squares) or SEQ ID NO:20 target (triangles) was 0.52 or 0.53, respectively. Similarly, when SEQ ID NO:18 circular oligonucleotide was mixed with a 1:1 combination both SEQ ID NO:19 and SEQ ID NO:20 targets (circles) the mole fraction circular oligonucleotide bound was 0.47 (FIG. 10B). Therefore, there was no significant difference in mole fraction of circular oligonucleotide bound when only one or when both targets were present. Accordingly, the stoichiometry of circular oligonucleotide to target in the hybridized complex was 1:1 whether one or both targets were present. These data indicate that the circular oligonucleotide undergoes a conformational charge upon binding and that a single target is bound. These data further indicate and that binding of both targets by a single SEQ ID NO:18 circular oligonucleotide is precluded.

Accordingly, when binding domain pair I bound its target oligonucleotide, the P and AP domains of pair II served as loop domains between the parallel and anti-parallel binding domains of pair I. Similarly, when binding domain pair II bound its target, the P and AP domains of pair I served as loop domains separating the parallel and anti-parallel binding domains of pair II. These two binding arrangements are depicted in FIG. 11A.

FIG. 13A depicts the absorbance versus mole fraction of SEQ ID NO:18 circular oligonucleotide present in a mixture with the longer two-target site oligonucleotide having SEQ ID NO:21. The mole fraction of circular oligonucleotide at complete complexation is about 0.63. This roughly corresponds to a stoichiometry of two circular oligonucleotides per target. Therefore separate circular oligonucleotides can bind to each of the two target binding sites present in the SEQ ID NO:21 oligonucleotide.

The complexes formed between circular oligonucleotide with SEQ ID NO:18 and targets having SEQ ID NO:19 or SEQ ID NO:20 were considerably stronger than corresponding complexes formed between a linear single binding domain oligonucleotide and target. For example, a nine base duplex formed between $d(A)_9$ (i.e. SEQ ID NO:20) and $d(T)_9$ (i.e. SEQ ID NO:23) had a $T_m$ of 25° C. and a duplex formed between $d(AG)_4A$ (i.e. SEQ ID NO:19) and $d(TC)_4T$ (i.e. SEQ ID NO:22) had a $T_m$ of 29° C. Therefore, the SEQ ID NO:18 circular oligonucleotide formed complexes with $T_m$ values that were at least 15° C. higher than corresponding linear duplex complexes. These results are summarized in Table 7 below. Given the high $T_m$ values and the 1:1 stoichiometry of the SEQ ID NO:18 oligonucleotide-target complexes, the complexes formed were triple-helical, and not double-helical.

TABLE 7

| $T_m$ VALUES OF LINEAR OLIGONUCLEOTIDES BOUND TO DIFFERENT TARGETS AT NEUTRAL pH | | |
|---|---|---|
| LINEAR OLIGONUCLEOTIDE | TARGET OLIGONUCLEOTIDE | $T_m$ |
| $d(TC)_4T$ (SEQ ID NO:22) | $d(AG)_4A$ (SEQ ID NO: 19) | 29° C. |
| $d(T)_9$ (SEQ ID NO:23) | $d(A)_9$ (SEQ ID NO:20) | 25° C. |
| $T_m$ VALUES OF THE SEQ ID NO:18 CIRCULAR OLIGONUCLEOTIDE BOUND TO DIFFERENT TARGETS AT NEUTRAL pH | | |
| CIRCULAR OLIGNUCLEOTIDE | TARGET OLIGONUCLEOTIDE | $T_m$ |
| SEQ ID NO:18 | SEQ ID NO:19 | 44.5° C. |
| SEQ ID NO:18 | SEQ ID NO:20 | 47.5° C. | pH Dependence of SEQ ID NO:18 Circular Oligonucleotide Binding to SEQ ID NO:19 and SEQ ID NO:20 Target Oligonucleotides The observed $T_m$ for the SEQ ID NO:20 target bound to the SEQ ID NO:18 circular oligonucleotide did not vary greatly from pH 5.5 to 9.0 (FIG. 12, open circles). In particular the $T_m$ of this complex at pH 5.5 was 51.5° C. and at pH 9.0 the $T_m$ was 46° C. These data are consistent with triple-helical complexes having only T-A-T triads, which require no protonation changes to optimize binding (Morgan et al. 1968 J. Mol. Biol. 37: 63–80; Moser et al. 1987 Science 238: 645; and Rajagopal et al. 1989 Nature 339: 637).

In contrast, the observed $T_m$ for the SEQ ID NO:19 target bound to the SEQ ID NO:18 circular oligonucleotide varied significantly over a range of 30° C. when the pH was varied from 5.5 to 9.0 (FIG. 12, open squares). In particular, at pH 5.5 the $T_m$ of the SEQ ID NO:19 Target-SEQ ID NO:18 circular oligonucleotide complex was 65° C. However at pH 9.0 the same complex has a $T_m$ of 35° C. These observations are consistent with previous observations that efficient formation of a C-G-C triad requires protonation of the cytosine in the parallel binding domain (Lipsett et al. 1963 Biochem. Biophys. Res. Comm. 11: 224–228 and Morgan et al. 1968).

Therefore, at pH 5.5 the complex having C-G-C triads (i.e. target SEQ ID NO:19 bound to SEQ ID NO:18 circular oligonucleotide) had a $T_m$ which was about 14° C. higher than the complex having only T-A-T triads (i.e. target SEQ ID NO:19 bound to SEQ ID NO:18 circular oligonucleotide). However at pH 9.0 the $T_m$ of the C-G-C triad containing complex was about 13° C. lower than the T-A-T triad containing complex. The pH of $T_m$ equivalency for the C-G-C and T-A-T containing complexes was pH 6.8.

pH Dependence of SEQ ID NO:18 Circular Oligonucleotide Binding to the Two-Target Site SEQ ID NO:21 Oligonucleotide The effect of pH upon binding of the SEQ ID NO:18 circular oligonucleotide with the longer two-target site oligonucleotide having SEQ ID NO:21 was also observed. FIG. 13B depicts the observed $T_m$ values for two molar equivalents SEQ ID NO:18 circular oligonucleotide bound to the SEQ ID NO:21 target. As shown, there were two $T_m$ values at each of the pH values tested. These two $T_m$ values correspond to separate melting events at each of the two target sites within the SEQ ID NO:21 oligonucleotide. Moreover the pattern of observed $T_m$ values for the SEQ ID NO:21 oligonucleotide parallels the pattern of $T_m$ values observed separately for the SEQ ID NO:19 and SEQ ID NO:20 target oligonucleotides. Therefore, each of the two $T_m$ values observed at a single pH for the SEQ ID NO:21 oligonucleotide can be assigned to a specific target site within this oligonucleotide. For example, at pH 5.5, $T_m$ values of 47° C. and 67° C. were observed for the SEQ ID NO:21 oligonucleotide. The $T_m$ values for the SEQ ID NO:19 and SEQ ID NO:20 targets were 65° C. and 51.5° C. respectively. Therefore the 47° C. $T_m$ value observed at pH 5.5 for the SEQ ID NO:21 oligonucleotide corresponds to the target encoding the same sequence as SEQ ID NO:20, i.e. (5'-dAAAAAAAAA). Similarly the 67° C. $T_m$ value observed at pH 5.5 for the SEQ ID NO:21 oligonucleotide corresponds to the target encoding the same sequence as SEQ ID NO:19, i.e. (5'-dAGAGAGAGA).

Therefore, the melting of each target within the SEQ ID NO:21 oligonucleotide can be separately observed and monitored at pH values ranging from 5.5 to 9.0.

Modulation of pH Can Selectively Direct Circular Oligonucleotide Binding to One Target vs Another The melting of varying amounts of the SEQ ID NO:18 circular oligonucleotide from the two-target site SEQ ID NO:21 oligonucleotide was monitored by observing the absorbance at 260 nm as the temperature was increased (FIG. 14). A sharp increase in the absorbance at this wavelength indicates that melting has occurred and provides a $T_m$ value for the SEQ ID NO:18-SEQ ID NO:21 complex at a given pH. These data also indicate which target site within the SEQ ID NO:21 oligonucleotide is occupied first by the circular oligonucleotide.

For example, FIG. 14A depicts the absorbance changes occurring as temperature is increased at pH 5.5 when the SEQ ID NO:21 oligonucleotide was present at 1.5 μM and the SEQ ID NO:18 circular oligonucleotide concentration was present at 0, 0.25, 0.5, 1.0 and 2.0 molar equivalents (lower to upper curves, respectively).

At low molar ratios of circular oligonucleotide (0.25, 0.50 and 1.0) a single sharp increase in absorbance was observed when the temperature was about 63° C. to 64° C. (FIG. 14A, middle three curves). This $T_m$ of about 63° C. to 64° C. indicates that melting is occurring from the SEQ ID NO:21 target site having the sequence AGAGAGAGA. Therefore at pH 5.5 when the proton concentration is relatively high, the target site having guanine residues is occupied first since formation of C-G-G triads is favored over formation of T-A-T triads.

However, when the circular oligonucleotide is present at 2.0 molar equivalents relative to the SEQ ID NO:21 oligonucleotide, two sharp increases in absorbance are apparent at pH 5.5 (FIG. 14A highest curve). Therefore when a molar excess of the circular oligonucleotide is present both target sites in the SEQ ID NO:21 oligonucleotide can be occupied by separate circular oligonucleotides.

At a higher pH of 8.5, when fewer protons are available, the observed $T_m$ at low molar ratios of circular oligonucleotide to SEQ ID NO:21 oligonucleotide, is significantly lower than observed at pH 5.5, i.e. about 52° C. (FIG. 14B middle three curves, corresponding to molar ratios of SEQ ID NO:18 to SEQ ID NO:21 oligonucleotide of 0.25, 0.5 and 1.0). A $T_m$ of about 52° C. indicates that melting is occurring from the target site encoding AAAAAAAA. Therefore at pH 8.5 the target site having only adenine residues is occupied first since the low concentration of protons makes formation of C-G-C triads less favorable than formation of T-A-T triads.

Addition of linear oligonucleotides having SEQ ID NO:22 (5'-dTCTCTCTCT) or SEQ ID NO:23 (5'-dTTTTTTTTT) confirmed that one target within the SEQ ID NO:21 oligonucleotide was unbound and the other target was bound by the SEQ ID NO:18 circular oligonucleotide at low pH. FIG. 15 depicts the hyperchromicity at pH 5.5 of a mixture of circular oligonucleotide (SEQ ID NO:18 at 1.5 μM) with two-target site oligonucleotide (SEQ ID NO:21 at 1.5 μM) in the presence of oligonucleotides having either SEQ ID NO:22 (TCTCTCTCT at 1.5 μM, filled circles) or SEQ ID NO:23 (TTTTTTTTT at 1.5 μM, open circles). At this low pH only the mixture of oligonucleotides having SEQ ID NO:18, 21 and 23 (open circles) had two melting temperatures, indicating that the SEQ ID NO:18 circular oligonucleotide bound to the AGAGAGAGA target site within the SEQ ID NO:21 oligonucleotide leaving the AAAAAAAA target site free for binding with the SEQ ID NO:23 oligonucleotide. Addition of the SEQ ID NO:22 oligonucleotide at pH 5.5 did not cause two melting events since this oligonucleotide was complementary to the target preferred by the circular oligonucleotide at low pH, i.e. the AGAGAGAGA target wherein C+G—C triads form. Accordingly, only one target site within the SEQ ID NO:21 oligonucleotide was occupied and only a single inflection in the hyperchromicity was observed (FIG. 15 filled circles).

Therefore, a circular oligonucleotide having two pairs of binding domains can be directed to bind one target as opposed to another by adjusting the pH of the hybridization reaction when one pair of binding domains contains more cytosine residues than the other pair.

What is claimed:

1. A method of preparing a single-stranded circular oligonucleotide comprising binding a linear precircle to an end-joining-oligonucleotide, joining two ends of said precircle and recovering said single-stranded circular oligonucleotide;

wherein said single-stranded circular oligonucleotide comprises at least one parallel binding (P) domain and at least one anti-parallel binding (AP) domain having a loop domain between each binding domain to form said circular oligonucleotide; each P and corresponding AP domain having sufficient complementarity to detectably bind to one strand of a defined nucleic acid target wherein said P domain binds in a parallel manner to said target, and said corresponding AP domain binds in an anti-parallel manner to said target.

2. The method of claim 1 wherein said linear precircle has a 3'-phosphate and a 5'-OH.

3. The method of claim 2 wherein said two ends are AP nucleotides of said single-stranded circular oligonucleotide.

4. The method of claim 3 wherein said joining is performed with BrCN, 1-ethyl-3-(3-dimethylaminopropyl) carbodiimide or N-cyanoimidazole ZnCl$_2$.

5. The method of claim 1 wherein said target comprises a known nucleotide sequence from which a nucleotide sequence for a sufficient number of positions in said P domain and a sufficient number of positions in said AP domain is determined, and wherein, for said P domain:

when a base for a position in said target is guanine or a guanine analog, then P has cytosine, or a suitable analog thereof, in a corresponding position;

when a base for a position in said target is adenine, or an adenine analog then P has thymine or uracil, or suitable analogs thereof, in a corresponding position;

when a base for a position in said target is thymine, or a thymine analog, then P has cytosine or guanine, or suitable analogs thereof, in a corresponding position;

when a base for a position in said target is cytosine, or a cytosine analog, then P has cytosine, thymine or uracil, or suitable analogs thereof, in a corresponding position; and when a base for a position in said target is uracil, or a uracil analog, then P has cytosine, guanine, thymine or uracil, or suitable analogs thereof, in a corresponding position;

and for said AP domain:

when a base for a position in said target is guanine, or a guanine analog, then AP has cytosine or uracil, or suitable analogs thereof, in a corresponding position;

when a base for a position in said target is adenine, or an adenine analog, then AP has thymine or uracil, or suitable analogs thereof, in a corresponding position;

when a base for a position in said target is thymine, or a thymine analog, then AP has adenine, or a suitable analog thereof, in a corresponding position;

when a base for a position in said target is cytosine, or a cytosine analog, then AP has a guanine, or a suitable analog thereof, in corresponding position; and when a base for a position in said target is uracil, or a uracil analog, then AP has adenine or guanine, or suitable analogs thereof, in a corresponding position; and wherein said sufficient number of positions provide complementarity for said oligonucleotide to detectably bind to said target.

6. The method of claim 1 wherein said P domain comprises a nucleotide sequence which is determined from a known nucleotide sequence of said target:

when a base for a position in said target is guanine or a guanine analog, then P has cytosine, or a suitable analog thereof, in a corresponding position;

when a base for a position in said target is adenine, or an adenine analog then P has thymine or uracil, or suitable analogs thereof, in a corresponding position;

when a base for a position in said target is thymine, or a thymine analog, then P has cytosine or guanine, or suitable analogs thereof, in a corresponding position;

when a base for a position in said target is cytosine, or a cytosine analog, then P has cytosine, thymine or uracil, or suitable analogs thereof, in a corresponding position; and when a base for a position in said target is uracil, or a uracil analog, then P has cytosine, guanine, thymine or uracil, or suitable analogs thereof, in a corresponding position;

and wherein said AP domain comprises a nucleotide sequence which is determined from said sequence of said target as follows:

when a base for a position in said target is guanine, or a guanine analog, then AP has cytosine or uracil, or suitable analogs thereof, in a corresponding position;

when a base for a position in said target is adenine, or an adenine analog, then AP has thymine or uracil, or suitable analogs thereof, in a corresponding position;

when a base for a position in said target is thymine, or a thymine analog, then AP has adenine, or a suitable analog thereof, in a corresponding position;

when a base for a position in said target is cytosine, or a cytosine analog, then AP has a guanine, or a suitable analog thereof, in corresponding position; and when a base for a position in said target is uracil, or a uracil analog, then AP has adenine or guanine, or suitable analogs thereof, in a corresponding position.

* * * * *

UNITED STATES PATENT AND TRADEMARK OFFICE
CERTIFICATE OF CORRECTION

PATENT NO. : 5,426,180
DATED : June 20, 1995
INVENTOR(S) : Eric T. Kool

It is certified that error appears in the above-indentified patent and that said Letters Patent is hereby corrected as shown below:

Column 5, lines 50-51: delete "rate constant, $K_{obs}$ for duplex target (SEQ ID NO:"

Column 21, line 12: after "because" delete --.--

Column 21, line 24: "Detection-can" should read --Detection can--

Column 24, line 57: "poly (A)" should read --poly(A)--

Column 29, line 30: "100 mM NiCl" should read --100 mM $NiCl_2$--

Column 29, line 51: "5,1SEQ" should read --5, SEQ--

Column 35, line 10: "A12" should read --$A_{12}$--

Column 37, line 65: "T" should read --$\underline{T}$--

Column 37, line 67: "U" should read --$\underline{U}$--

Column 40, line 5: "8 5 X 10" should read --8.5 X 10--

UNITED STATES PATENT AND TRADEMARK OFFICE
CERTIFICATE OF CORRECTION

PATENT NO. : 5,426,180

DATED : June 20, 1995

INVENTOR(S) : Eric T. Kool

It is certified that error appears in the above-indentified patent and that said Letters Patent is hereby corrected as shown below:

Column 40, line 49: "1981Tetrahedron" should read --1981 Tetrahedron--

Column 41, lines 21-22:
" 5'-dCACAAGAGAGAGAATCCCTAAAAAAAAAAACAC " should read
-- 5'-dCACAAGAGAGAGAATCCCTAAAAAAAAAAACAC --

Column 42, line 19: "be-less" should read --be less--

Column 42, line 20: "0.3.3" should read --0.33--

Column 43, lines 61-62: "Blo-chem." should read --Bio-chem.--

Signed and Sealed this

Sixteenth Day of April, 1996

BRUCE LEHMAN

*Attest:*

*Attesting Officer*     *Commissioner of Patents and Trademarks*

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: circular ( i i ) MOLECULE TYPE: DNA ( x i ) SEQUENCE DESCRIPTION: SEQ ID NO:1:

```
CTCCCCGCCC  TCNNNNNCTC  CCACCCCTCN  NNNN                        3 4
```

( 2 ) INFORMATION FOR SEQ ID NO:2:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: circular ( i i ) MOLECULE TYPE: DNA ( x i ) SEQUENCE DESCRIPTION: SEQ ID NO:2:

```
TCTTTTTCT  TTTCNNNNNC  TTTCTTTTT  TCTNNNNN                       3 8
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: circular ( i i ) MOLECULE TYPE: DNA ( x i ) SEQUENCE DESCRIPTION: SEQ ID NO:3:

```
TTTCYTCGTT CGTCNNNNNC TACTTACTGC TTTNNNNN                    38
```

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: circular ( i i ) MOLECULE TYPE: DNA ( x i ) SEQUENCE DESCRIPTION: SEQ ID NO:4:

```
TCCTTCTTCY CCTCTNNNNN TCTCCGCTTC TTCCTNNNNN                  40
```

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( i i ) MOLECULE TYPE: DNA ( x i ) SEQUENCE DESCRIPTION: SEQ ID NO:5:

```
TTTTTCACA CTTTTTTTT TTTCACACTT TTTT                          34
```

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( i i ) MOLECULE TYPE: DNA ( x i ) SEQUENCE DESCRIPTION: SEQ ID NO:6:

```
TCTTTCCACA CCTTTCTTTT CTTCACACTT CTTT                        34
```

( 2 ) INFORMATION FOR SEQ ID NO:7:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: both ( i i ) MOLECULE TYPE: DNA ( x i ) SEQUENCE DESCRIPTION: SEQ ID NO:7:

```
TTTCTTCACA CTTCTTTTCT TTCCACACCT TTCT                        34
```

( 2 ) INFORMATION FOR SEQ ID NO:8:

( i ) SEQUENCE CHARACTERISTICS:
        ( A ) LENGTH: 12 base pairs
        ( B ) TYPE: nucleic acid
        ( C ) STRANDEDNESS: single ( D ) TOPOLOGY: linear ( i i ) MOLECULE TYPE: DNA ( x i ) SEQUENCE DESCRIPTION: SEQ ID NO:8:

AAAAAAAAAA AA                                                                                           12

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

AAGAAAGAA AG                                                                                            12

( 2 ) INFORMATION FOR SEQ ID NO:10:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

CTTTCTTTTC TT                                                                                           12

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

AAGAATAGAA AG                                                                                           12

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

AAGAAUAGAA AG                                                                                           12

( 2 ) INFORMATION FOR SEQ ID NO:13:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

TTCTTATCTT TC                                                                                           12

( 2 ) INFORMATION FOR SEQ ID NO:14:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: both ( i i ) MOLECULE TYPE: DNA ( x i ) SEQUENCE DESCRIPTION: SEQ ID NO:14:

TTCTTCTCTT TCCACACCTT TCTATTCTTC ACAC      3 4

( 2 ) INFORMATION FOR SEQ ID NO:15:

( i ) SEQUENCE CHARACTERISTICS:
    ( A ) LENGTH: 12 base pairs
    ( B ) TYPE: nucleic acid
    ( C ) STRANDEDNESS: double
    ( D ) TOPOLOGY: linear ( i i ) MOLECULE TYPE: DNA ( x i ) SEQUENCE DESCRIPTION: SEQ ID NO:15:

AAAAAAAAAA AA      1 2

( 2 ) INFORMATION FOR SEQ ID NO:16:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:16:

TCTCTTTTTT TTTTCTCTC TCTTTTTTTT TTTCTC      3 6

( 2 ) INFORMATION FOR SEQ ID NO:17:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:17:

AAAGAGAGAG AAA      1 3

( 2 ) INFORMATION FOR SEQ ID NO:18:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: circular ( i i ) MOLECULE TYPE: DNA ( x i ) SEQUENCE DESCRIPTION: SEQ ID NO:18:

TTTTTTTTTT CTCTCTCTTT TTTTTTTTCT CTCTCT      3 6

( 2 ) INFORMATION FOR SEQ ID NO:19:

( i ) SEQUENCE CHARACTERISTICS:
    ( A ) LENGTH: 9 base pairs
    ( B ) TYPE: nucleic acid ( C ) STRANDEDNESS: single
        ( D ) TOPOLOGY: linear ( i i ) MOLECULE TYPE: DNA ( x i ) SEQUENCE DESCRIPTION: SEQ ID NO:19:

AGAGAGAGA                                                                                   9

( 2 ) INFORMATION FOR SEQ ID NO:20:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

AAAAAAAAA                                                                                   9

( 2 ) INFORMATION FOR SEQ ID NO:21:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

CACAAGAGAG AGAATCCCTA AAAAAAAAA CAC                                                        33

( 2 ) INFORMATION FOR SEQ ID NO:22:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

TCTCTCTCT                                                                                   9

( 2 ) INFORMATION FOR SEQ ID NO:23:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:23:

TTTTTTTTT                                                                                   9